US012720264B1

(12) United States Patent
Rapoport

(10) Patent No.: US 12,720,264 B1
(45) Date of Patent: Aug. 25, 2026

(54) EAR-ASSOCIATED INERTIAL-ACOUSTIC FUSION WITH DETERMINISTIC AUDIO-IMU SYNCHRONIZATION

(71) Applicant: Uri Benjamin Rapoport, Moshav Ben Shemen (IL)

(72) Inventor: Uri Benjamin Rapoport, Moshav Ben Shemen (IL)

(73) Assignee: VEXARA GMBH, Frankfurt am Main (DE)

( * ) Notice: Subject to any disclaimer, the term of this patent is extended or adjusted under 35 U.S.C. 154(b) by 0 days.

(21) Appl. No.: 19/548,036

(22) Filed: Feb. 24, 2026

Related U.S. Application Data

(60) Provisional application No. 63/917,286, filed on Nov. 14, 2025, provisional application No. 63/918,231, (Continued)

(51) Int. Cl.
*H04R 25/00* (2006.01)
*A61B 5/00* (2006.01)
(Continued)

(52) U.S. Cl.
CPC .......... *H04R 25/407* (2013.01); *A61B 5/1114* (2013.01); *A61B 5/6817* (2013.01); (Continued)

(58) Field of Classification Search
CPC .. H04R 25/407; H04R 25/552; H04R 25/603; H04R 25/604; H04R 2225/67; (Continued)

(56) References Cited

U.S. PATENT DOCUMENTS 9,107,001 B2 8/2015 Diethorn et al.
11,601,764 B2 3/2023 Benattar et al.
(Continued)

FOREIGN PATENT DOCUMENTS

EP 4207814 A1 7/2023
WO 2016124580 A1 8/2016

*Primary Examiner* — Tuan D Nguyen
(74) *Attorney, Agent, or Firm* — The Roy Gross Law Firm, LLC; Roy D. Gross

(57) ABSTRACT

An ear-associated assistive system is disclosed that integrates acoustic sensing and inertial sensing to generate motion-compensated spatial parameters for hearing assistance and, in certain embodiments, to control stimulation for implantable auditory and/or vestibular interfaces. The system maintains temporal alignment between inertial samples and audio samples by maintaining a deterministic mapping between inertial sample times and audio sample indices, including across power-state transitions, thereby enabling reliable sensor fusion and consistent outputs. In certain implementations, an ear-frame coordinate system is established based on fixed mechanical placement of an inertial sensing subsystem relative to one or more microphones, and calibration parameters are stored to align sensor axes, microphone geometry and latency. A processor computes a head-motion state from inertial data and transforms an ear-frame direction estimate derived from acoustic data into a stabilized direction parameter expressed in a stabilized coordinate frame, optionally outputting a quality metric indicative of validity. The stabilized direction parameter and/or quality metric may be used for beamforming, binaural rendering and routing. The system may further detect motion events and apply safety gating rules to mitigate motion artifacts and constrain acoustic output and/or stimulation, subject to safety constraints and, in certain embodiments, clinician-defined bounds. Interoperability with an external directional
(Continued)

accessory is also described, wherein inertial-acoustic fusion is used to stabilize directional operation and maintain consistent routing.

20 Claims, 15 Drawing Sheets

Related U.S. Application Data filed on Nov. 15, 2025, provisional application No. 63/918,234, filed on Nov. 15, 2025, provisional application No. 63/918,520, filed on Nov. 16, 2025, provisional application No. 63/923,184, filed on Nov. 22, 2025, provisional application No. 63/923,398, filed on Nov. 23, 2025, provisional application No. 63/927,441, filed on Nov. 29, 2025, provisional application No. 63/931,838, filed on Dec. 5, 2025, provisional application No. 63/955,419, filed on Jan. 7, 2026, provisional application No. 63/958,859, filed on Jan. 12, 2026, provisional application No. 63/958,867, filed on Jan. 12, 2026.

(51) Int. Cl.
*A61B 5/11* (2006.01)
*H04S 7/00* (2006.01)

(52) U.S. Cl.
CPC ......... *H04R 25/552* (2013.01); *H04R 25/603* (2019.05); *H04R 25/604* (2013.01); *H04S 7/304* (2013.01); *A61B 2562/0219* (2013.01); *H04R 2225/67* (2013.01); *H04S 2400/11* (2013.01)

(58) Field of Classification Search
CPC .... H04S 7/304; H04S 2400/11; A61B 5/1114; A61B 5/6817; A61B 2562/0219
See application file for complete search history.

(56) References Cited

U.S. PATENT DOCUMENTS

| | | | |
|---|---|---|---|
| 11,636,842 | B2 | 4/2023 | Carlile et al. |
| 2016/0080874 | A1 | 3/2016 | Fullam |
| 2022/0070567 | A1 | 3/2022 | Skoglund et al. |
| 2023/0260538 | A1 | 8/2023 | Inskip, VI et al. |

System 1000
Output Subsystem 1400
Acoustic Output Transducer 1410
Stimulation Interface 1420
Wireless Link 1600
Processor 1300
Fusion Engine 1310
Spatial Estimator 1320
Control Logic 1330
Synchronization Module 1500
Acoustic Transducer Subsystem 1100
Microphones 1110
Inertial Sensing Subsystem 1200
IMU 1200

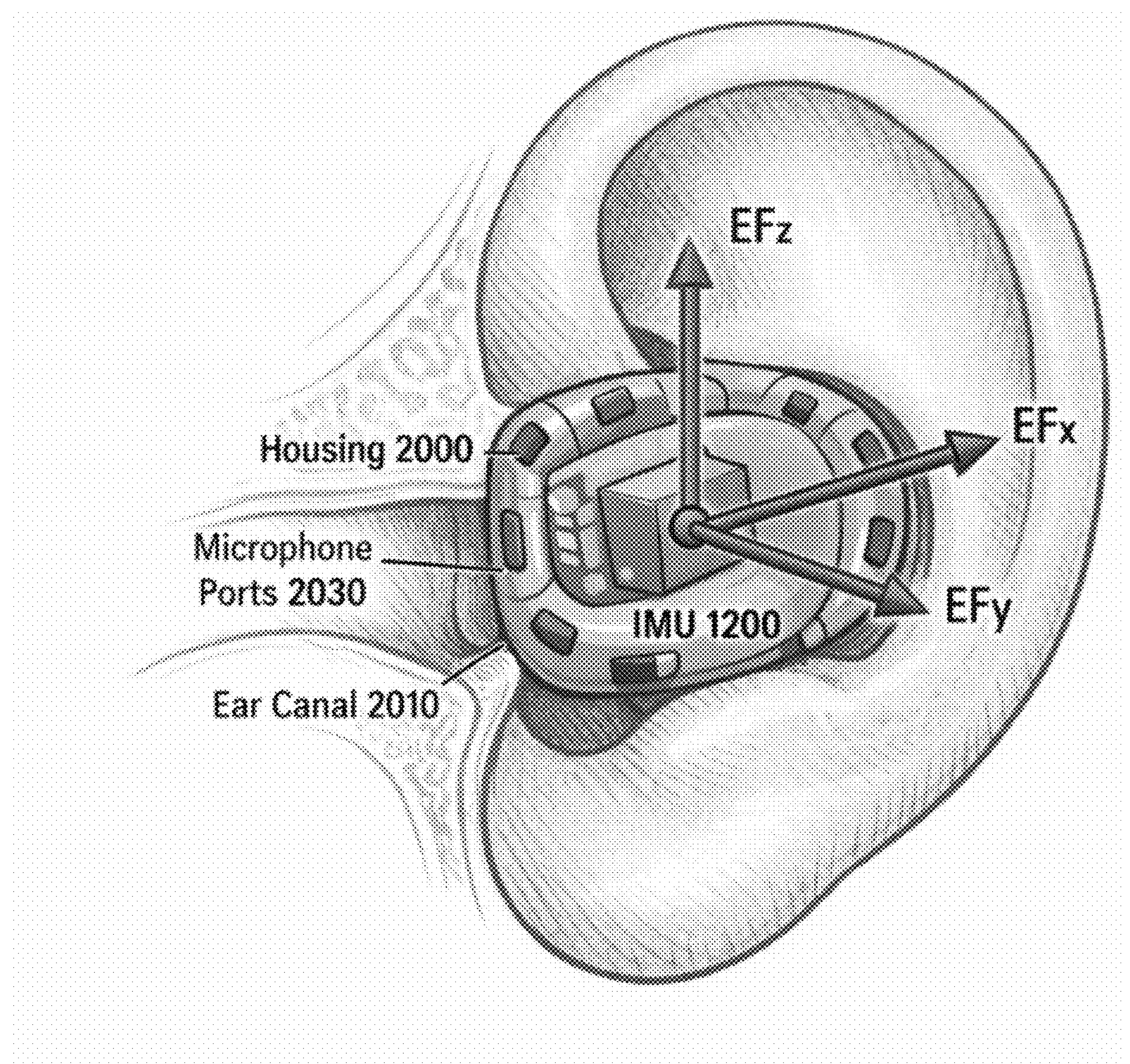
FIG. 2 Ear-Worn Mechanical Integration and Coordinate Definition

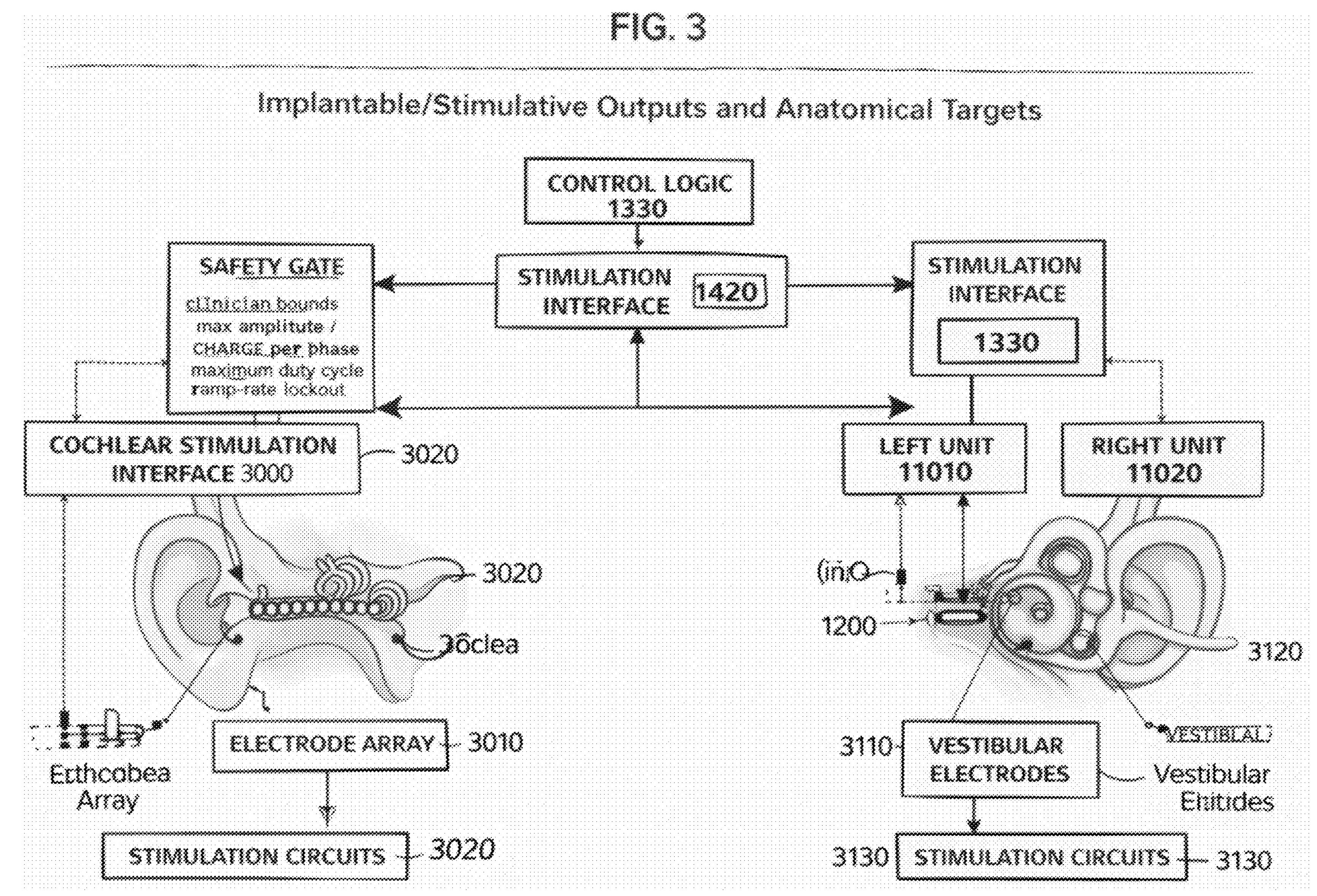
FIG. 3
Implantable/Stimulative Outputs and Anatomical Targets
CONTROL LOGIC 1330
SAFETY GATE
clinician bounds
max amplitude /
CHARGE per phase
maximum duty cycle
ramp-rate lockout
STIMULATION INTERFACE 1420
STIMULATION INTERFACE 1330
COCHLEAR STIMULATION INTERFACE 3000
3020
LEFT UNIT 11010
RIGHT UNIT 11020
3020
1200
3120
ELECTRODE ARRAY
3010
Erthcobea Array
VESTIBULAR ELECTRODES
3110
Vestibular Elctides
STIMULATION CIRCUITS
3020
3130
STIMULATION CIRCUITS
3130

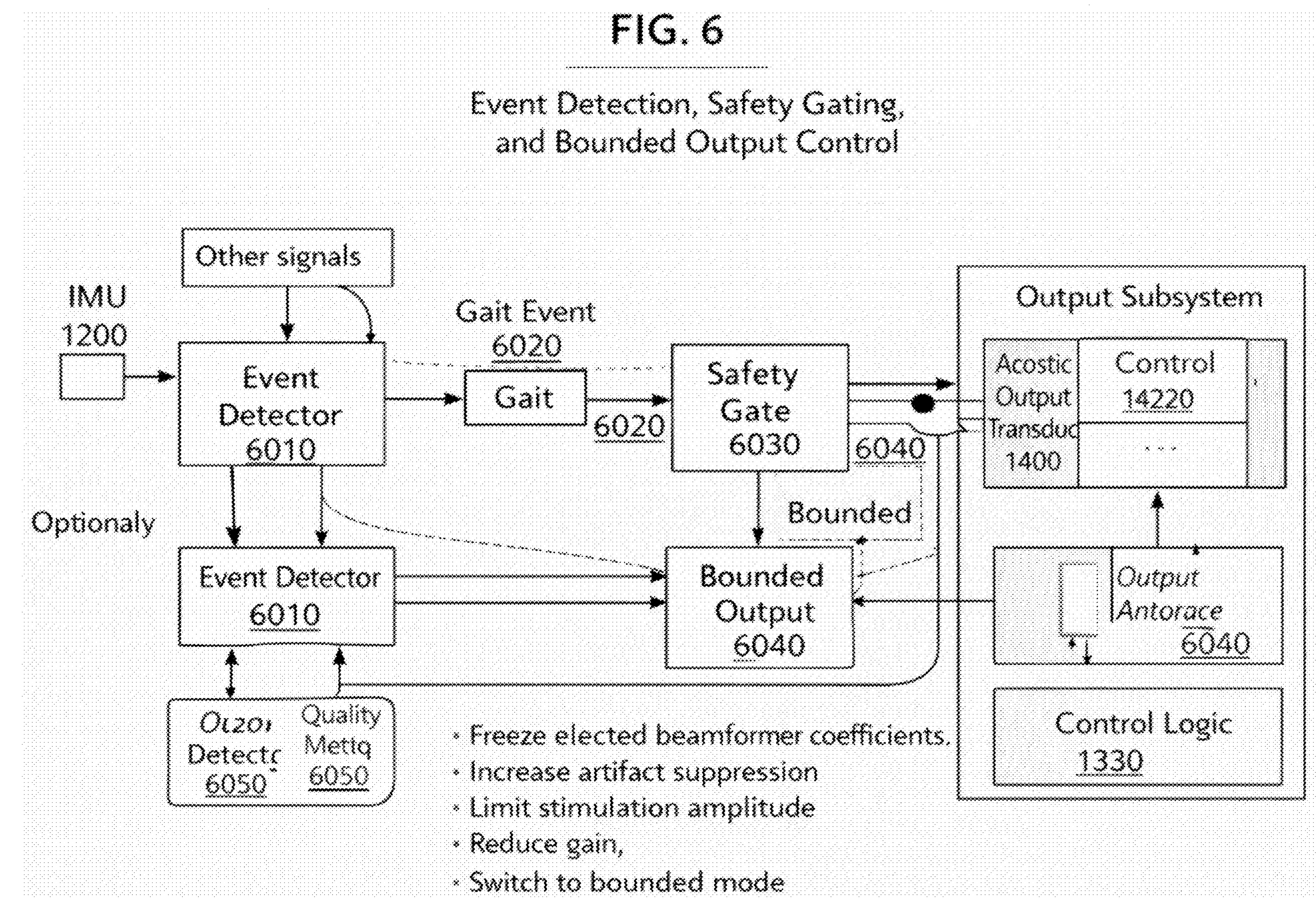
FIG. 6
Event Detection, Safety Gating, and Bounded Output Control
IMU 1200
Other signals
Event Detector 6010
Gait Event 6020
Gait
6020
Safety Gate 6030
6040
Bounded
Optionaly
Event Detector 6010
Bounded Output 6040
Output Subsystem
Acostic Output Transduc 1400
Control 14220
Output Antorace 6040
Control Logic 1330
Quality Metiq 6050
Detectc 6050
· Freeze elected beamformer coefficients.
· Increase artifact suppression
· Limit stimulation amplitude
· Reduce gain,
· Switch to bounded mode

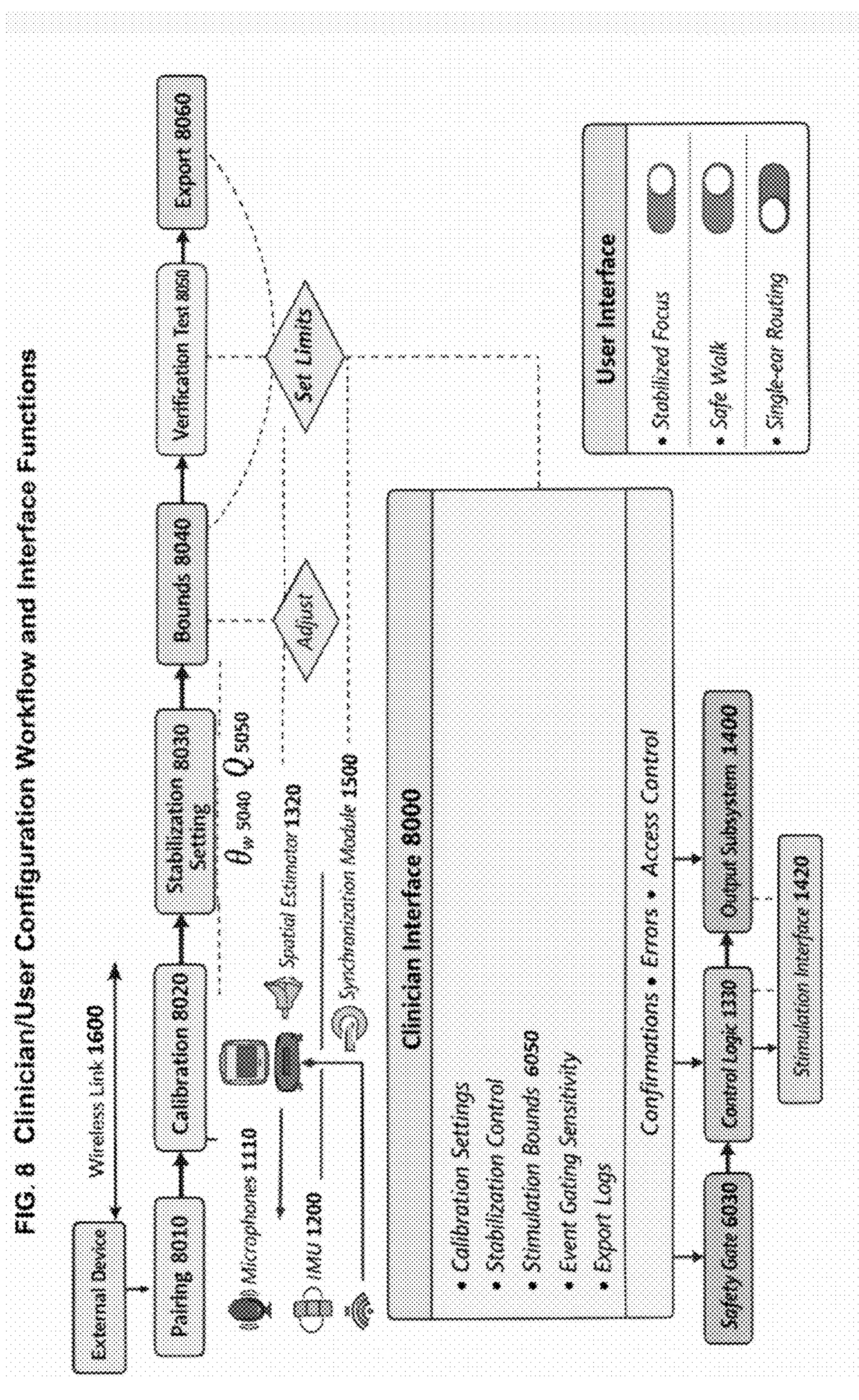
FIG. 8 Clinician/User Configuration Workflow and Interface Functions
External Device
Wireless Link 1600
Pairing 8010
Calibration 8020
Stabilization Setting 8030
Bounds 8040
Verification Test 8050
Export 8060
Adjust
Set Limits
$\theta_w$ 5040
$Q$ 5050
Microphones 1110
IMU 1200
Spatial Estimator 1320
Synchronization Module 1500
Clinician Interface 8000
• Calibration Settings
• Stabilization Control
• Stimulation Bounds 6050
• Event Gating Sensitivity
• Export Logs
Confirmations • Errors • Access Control
User Interface
• Stabilized Focus
• Safe Walk
• Single-ear Routing
Safety Gate 6030
Control Logic 1330
Output Subsystem 1400
Stimulation Interface 1420

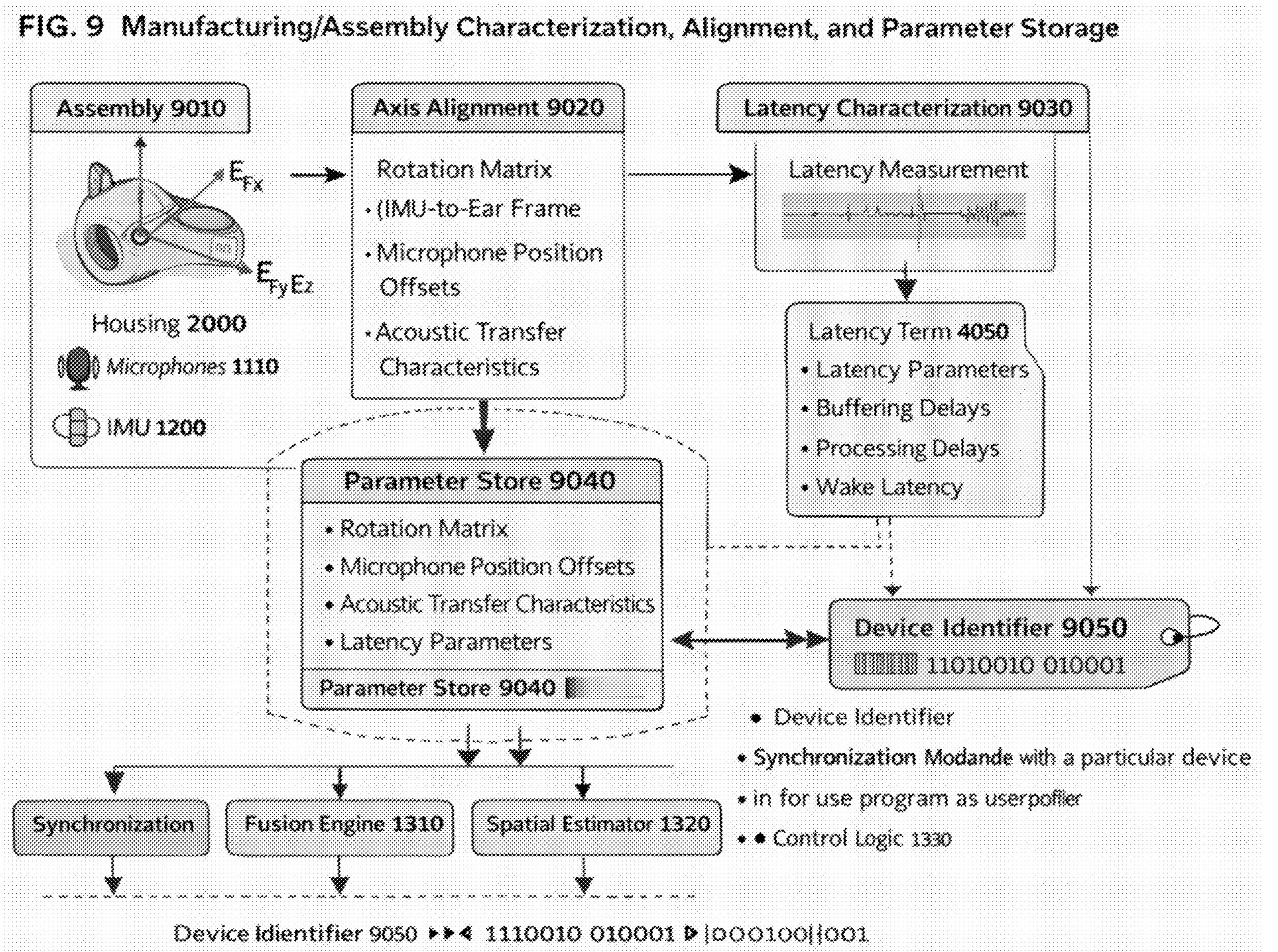
FIG. 9 Manufacturing/Assembly Characterization, Alignment, and Parameter Storage
Assembly 9010
$E_{Fx}$
$E_{Fy}$ $E_z$
Housing 2000
Microphones 1110
IMU 1200
Axis Alignment 9020
Rotation Matrix
· (IMU-to-Ear Frame
· Microphone Position Offsets
· Acoustic Transfer Characteristics
Latency Characterization 9030
Latency Measurement
Latency Term 4050
• Latency Parameters
• Buffering Delays
• Processing Delays
• Wake Latency
Parameter Store 9040
• Rotation Matrix
• Microphone Position Offsets
• Acoustic Transfer Characteristics
• Latency Parameters
Parameter Store 9040
Device Identifier 9050
11010010 010001
• Device Identifier
• Synchronization Modande with a particular device
• in for use program as userpofier
• • Control Logic 1330
Synchronization
Fusion Engine 1310
Spatial Estimator 1320
Device Idientifier 9050 1110010 010001

Method Flow for Synchronization, Estimation, Output Generation, and Logging

FIG. 11

External Accessory, Dual-Unit Coordination, and Direction/Gaze Stabilization

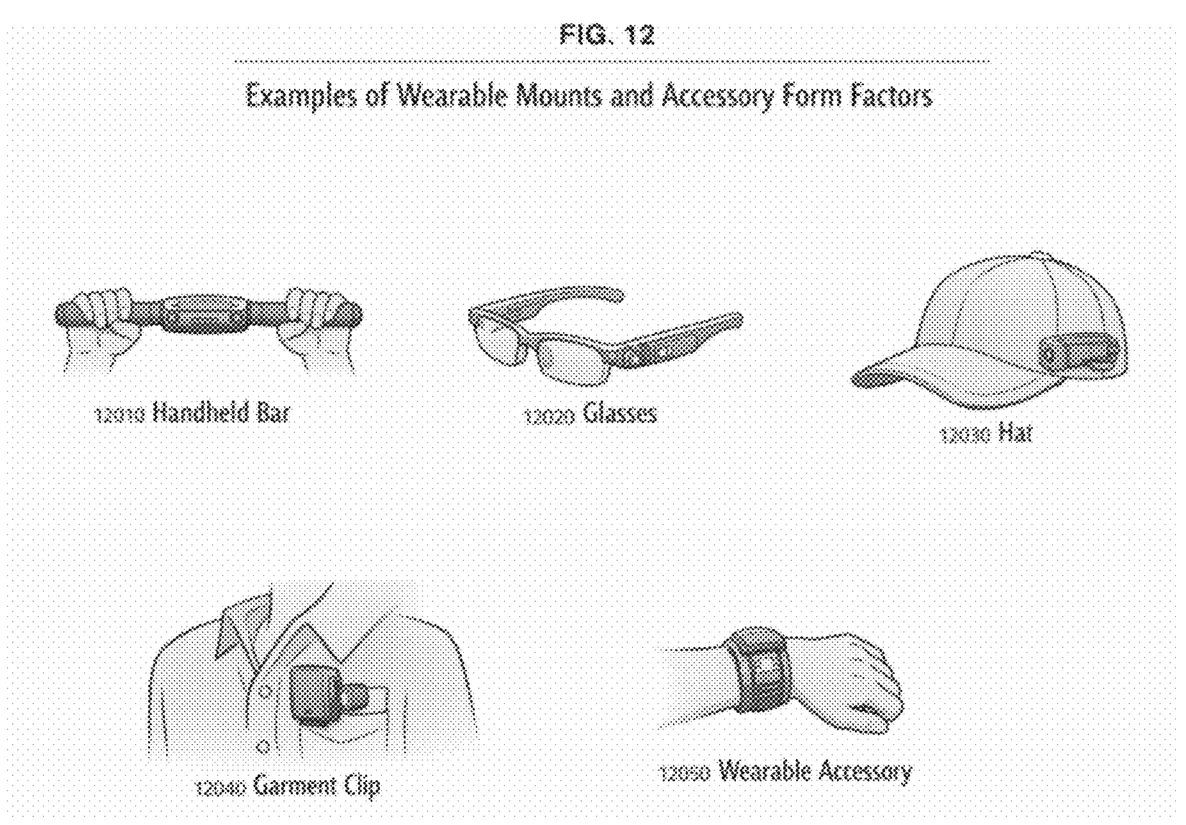
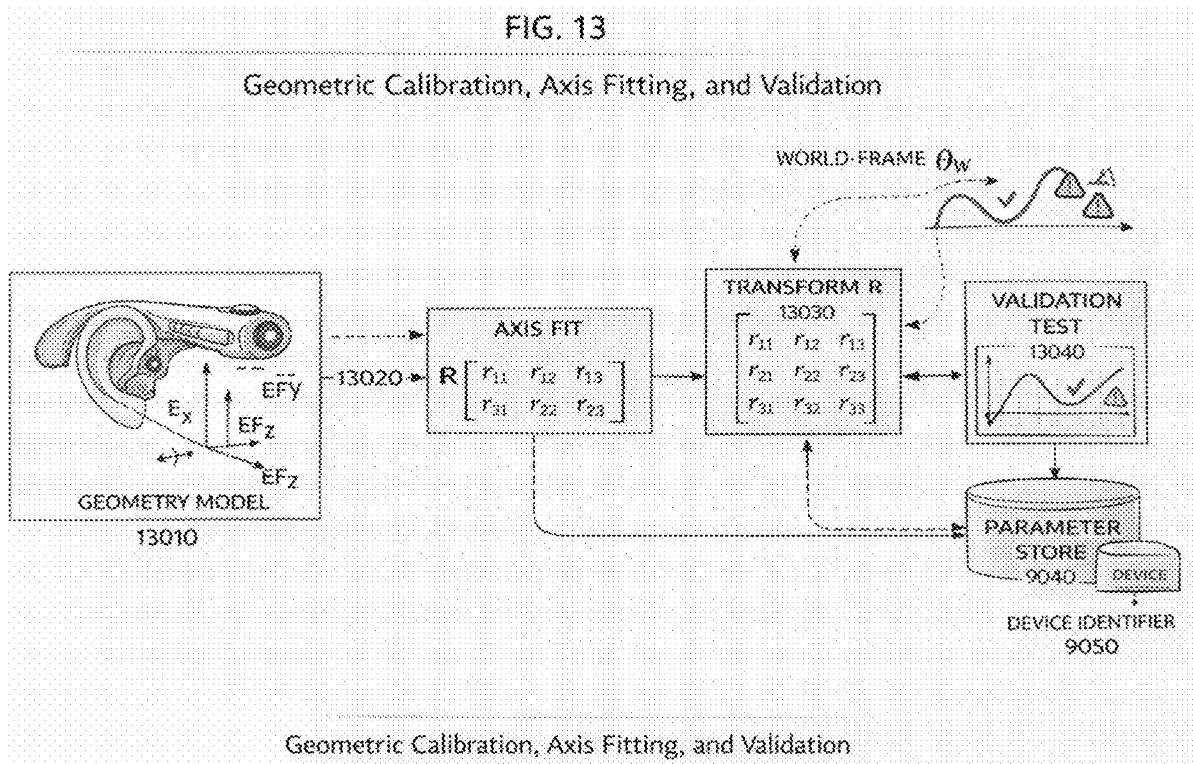
Geometric Calibration, Axis Fitting, and Validation

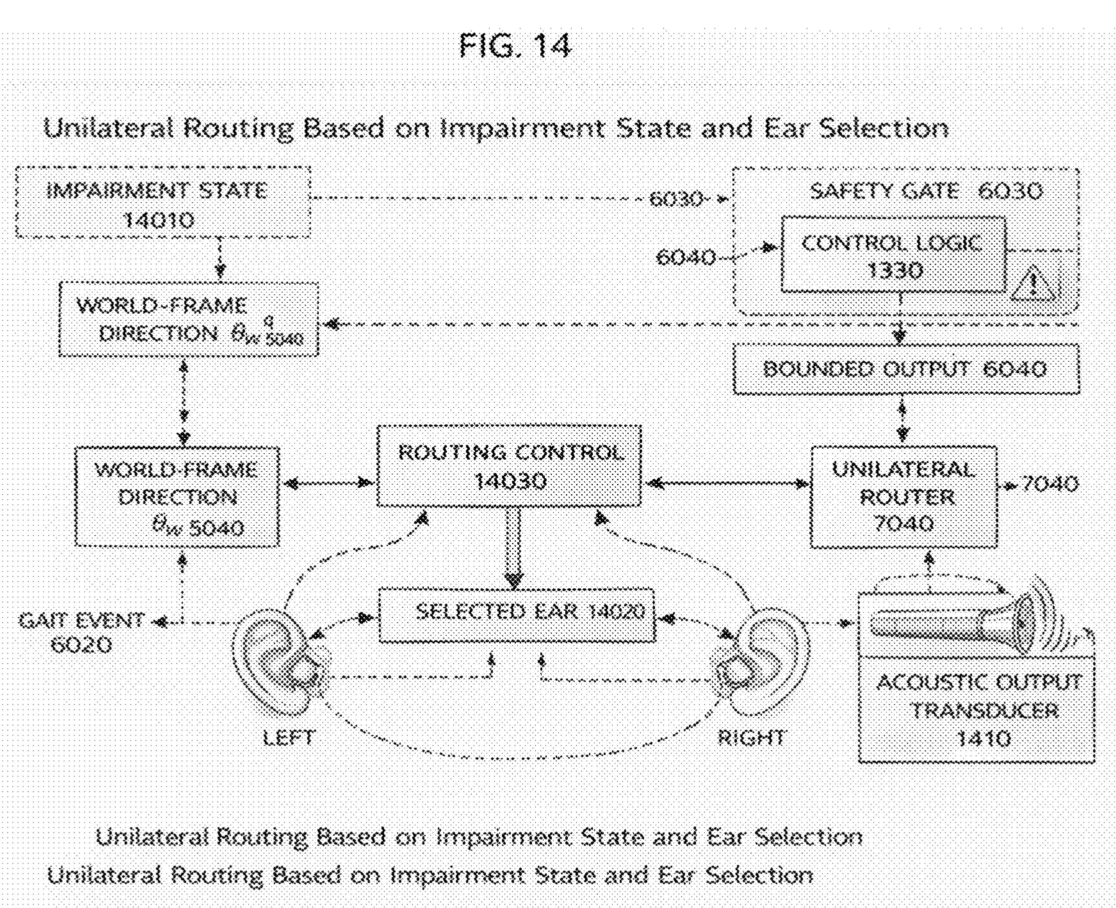
FIG. 14
Unilateral Routing Based on Impairment State and Ear Selection
IMPAIRMENT STATE
14010
6030
SAFETY GATE 6030
6040
CONTROL LOGIC
1330
WORLD-FRAME
DIRECTION $\theta_W^q$ 5040
BOUNDED OUTPUT 6040
WORLD-FRAME
DIRECTION
$\theta_W$ 5040
ROUTING CONTROL
14030
UNILATERAL
ROUTER
7040
7040
GAIT EVENT
6020
SELECTED EAR 14020
ACOUSTIC OUTPUT
TRANSDUCER
1410
LEFT
RIGHT
Unilateral Routing Based on Impairment State and Ear Selection
Unilateral Routing Based on Impairment State and Ear Selection

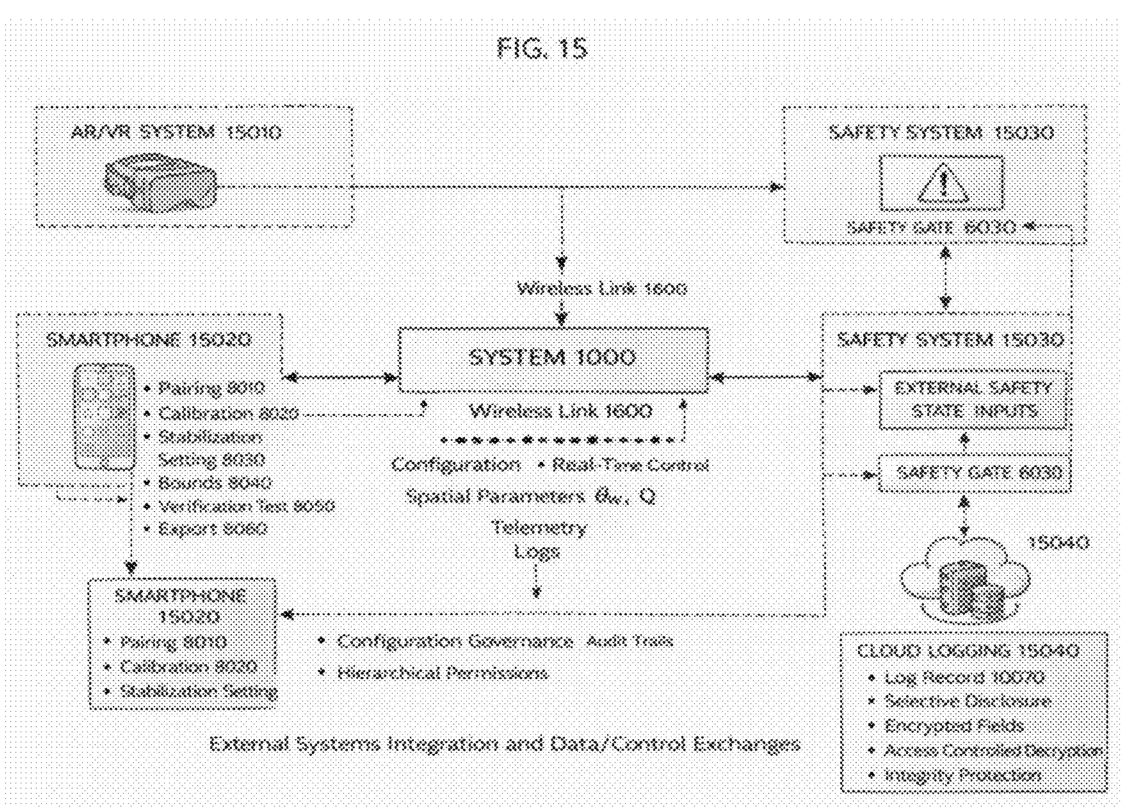
FIG. 15
AR/VR SYSTEM 15010
SAFETY SYSTEM 15030
SAFETY GATE 6030
Wireless Link 1600
SMARTPHONE 15020
• Pairing 8010
• Calibration 8020
• Stabilization
Setting 8030
• Bounds 8040
• Verification Test 8050
• Export 8060
SYSTEM 1000
Wireless Link 1600
Configuration • Real-Time Control
Spatial Parameters $\theta_W$, Q
Telemetry
Logs
SAFETY SYSTEM 15030
EXTERNAL SAFETY
STATE INPUTS
SAFETY GATE 6030
15040
SMARTPHONE
15020
• Pairing 8010
• Calibration 8020
• Stabilization Setting
• Configuration Governance Audit Trails
• Hierarchical Permissions
CLOUD LOGGING 15040
• Log Record 10070
• Selective Disclosure
• Encrypted Fields
• Access Controlled Decryption
• Integrity Protection
External Systems Integration and Data/Control Exchanges

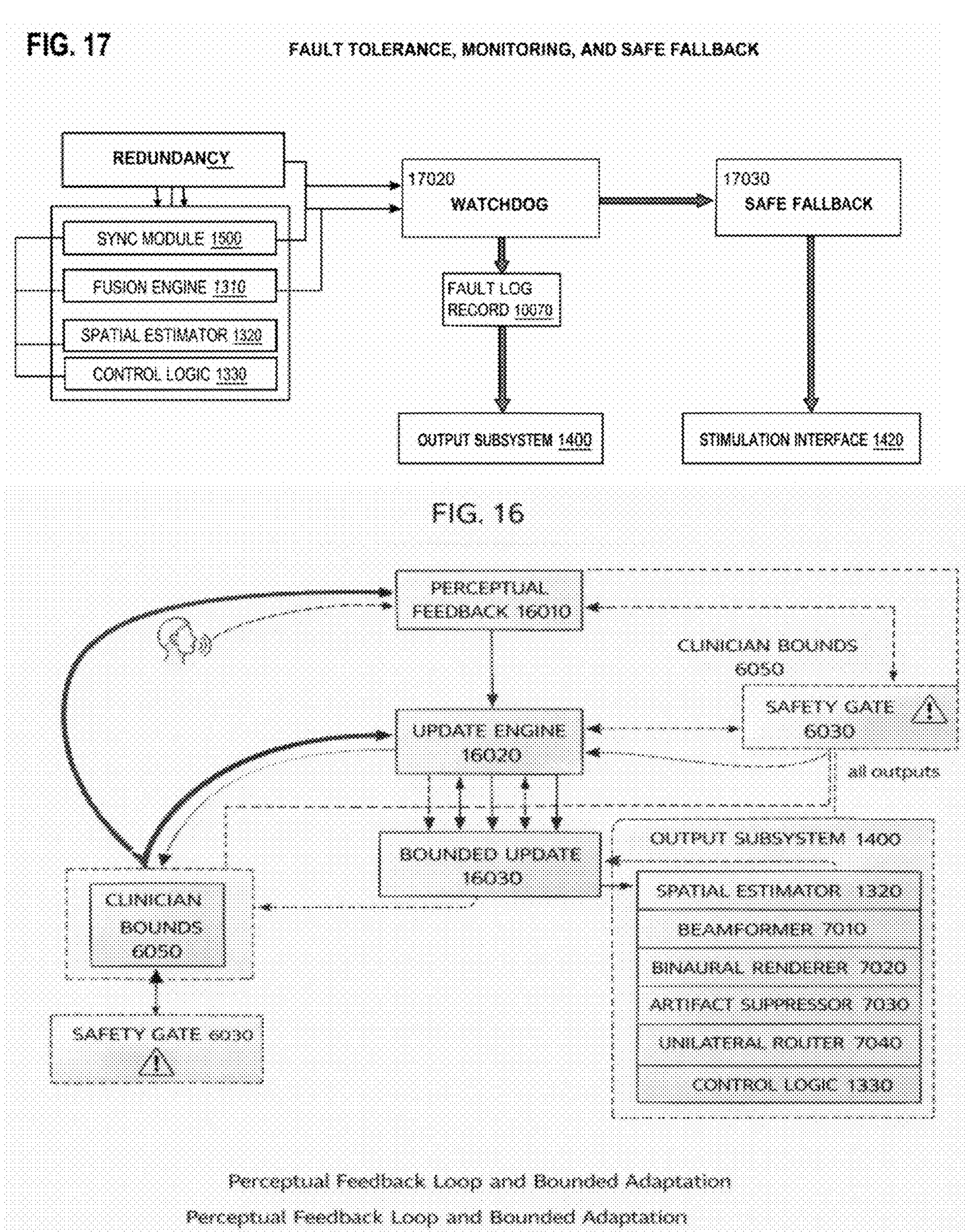
Perceptual Feedback Loop and Bounded Adaptation

EAR-ASSOCIATED INERTIAL-ACOUSTIC FUSION WITH DETERMINISTIC AUDIO-IMU SYNCHRONIZATION

CROSS REFERENCE TO RELATED APPLICATIONS

This application claims the benefit of priority of U.S. Provisional Patent Application Nos. 63/917,286 filed Nov. 14, 2025; 63/918,231 filed Nov. 15, 2025; 63/918,234 filed Nov. 15, 2025; 63/918,520 filed Nov. 16, 2025; 63/923,184 filed Nov. 22, 2025; 63/923,398 filed Nov. 23, 2025; 63/927,441 filed Nov. 29, 2025; 63/931,838 filed Dec. 5, 2025; 63/955,419 filed Jan. 7, 2026; 63/958,859 filed Jan. 12, 2026; and 63/958,867 filed Jan. 12, 2026. The contents of the aforementioned applications are all incorporated herein by reference in their entirety.

TECHNICAL FIELD AND BACKGROUND ART

The present invention relates to ear-associated assistive systems and, more particularly, to ear-worn and/or implantable hearing and balance systems that integrate inertial sensing and acoustic sensing to generate stabilized spatial parameters and/or stimulation control signals, while maintaining deterministic temporal alignment between inertial samples and audio samples, including during transitions between power states.

Hearing assistance devices and implants increasingly rely on spatial processing, adaptive filtering, and user-context inference. Separately, vestibular implants and vestibular stimulation systems are being investigated and deployed to treat vestibular dysfunction. Motion sensors have been proposed for both hearing and vestibular applications, including vestibular implant systems using internal and/or external motion sensors. However, known approaches commonly suffer from one or more of the following: (i) inadequate deterministic time alignment between audio sampling and inertial sampling, particularly across sleep/wake or power gating transitions; (ii) spatial processing drift under head motion due to imperfect mapping between an ear-frame coordinate system and a world-frame coordinate system; (iii) limited calibration between acoustic sensor geometry and inertial sensor axes; and/or (iv) insufficient safety gating for stimulation and/or overly aggressive filtering during transient motion events (e.g., steps, head impulses). Consumer head-tracked spatial audio demonstrates head-motion tracking for audio rendering but does not address clinical calibration, deterministic time mapping between sensor streams for assistive pipelines, or constraints applicable to closed-loop stimulation control. There therefore remains a long-felt and unmet need for an ear-associated assistive architecture that provides ear-frame inertial-acoustic fusion with deterministic synchronization and stabilized spatial outputs, optionally driving both acoustic output and vestibular and/or auditory stimulation, in a manner that is power-efficient, safe, and reproducible for clinical fitting and evidence-grade logging.

SUMMARY OF THE INVENTION

In one aspect, an ear-associated assistive system includes an acoustic transducer subsystem configured to generate an audio signal, an inertial sensing subsystem configured to generate inertial data indicative of head motion, an output subsystem configured to provide an output to a user, at least one processor operatively coupled thereto, and a synchronization module configured to maintain temporal alignment between the audio signal and the inertial data. The at least one processor determines, based on the audio signal and the inertial data, a motion-compensated spatial parameter and controls the output subsystem in dependence on the motion-compensated spatial parameter.

In certain implementations, the acoustic transducer subsystem includes one or more microphones and the inertial data includes at least angular rate. Temporal alignment may be deterministic and may include maintaining a deterministic mapping between inertial sample times and audio sample indices, including maintaining the deterministic mapping across a power-state transition. The processor may compute, from the inertial data, a head-motion state; compute, from the audio signal, an ear-frame direction parameter; and apply a transformation based on the head-motion state to obtain a stabilized direction parameter expressed in a stabilized coordinate frame, and control output generation based on the stabilized direction parameter.

In certain implementations, the inertial sensing subsystem is disposed within an in-ear or ear-worn housing that defines an ear-frame coordinate system.

In certain implementations, the processor outputs, together with the motion-compensated spatial parameter and/or the stabilized direction parameter, a quality metric indicative of validity, and enables, weights, or inhibits one or more downstream audio processing actions based on the quality metric.

In certain implementations, the processor controls a beamformer in dependence on the motion-compensated spatial parameter and/or the stabilized direction parameter to generate a beamformed signal for driving an acoustic output transducer.

In certain implementations, the output subsystem includes a stimulation interface comprising a cochlear stimulation interface including an electrode array and/or a vestibular stimulation interface configured to stimulate vestibular pathways. The processor may generate a stimulation control signal subject to one or more safety constraints, optionally including clinician-defined bounds, such as maximum amplitude, maximum charge per phase, maximum duty cycle, ramp-rate limit, and/or lockout behaviour.

In certain implementations, the processor detects a motion event from the inertial data and, in response to the motion event and/or a reduced quality metric, controls the output subsystem in accordance with a safety gating rule by limiting at least one of acoustic gain, beamformer adaptation, or stimulation amplitude, and optionally by freezing selected beamformer coefficients and/or increasing artifact suppression during the motion event.

In another aspect, a method of operating an ear-associated assistive system includes sampling an audio signal, sampling inertial data indicative of head motion, maintaining temporal alignment between the audio signal and the inertial data, determining a motion-compensated spatial parameter based on the audio signal and the inertial data, and controlling generation of at least one output in dependence on the motion-compensated spatial parameter. In certain implementations, the temporal alignment is deterministic and maintained across a power-state transition, and the motion-compensated spatial parameter includes a stabilized direction parameter derived by transforming an ear-frame direction parameter using a head-motion state computed from the inertial data.

In another aspect, a non-transitory computer-readable medium stores instructions that, when executed by at least one processor of an ear-associated assistive system, cause the processor to perform the disclosed methods, including storing calibration parameters and computing and/or updating the deterministic mapping based on at least a latency parameter.

In another aspect, a combined assistive system includes the ear-associated assistive system and an external binaural steering accessory having left and right acoustic units, wherein the processor stabilizes directional operation of the accessory in the stabilized coordinate frame based on the stabilized direction parameter, and optionally calibrates a transformation between accessory geometry and the ear-frame coordinate system

BRIEF DESCRIPTION OF THE DRAWINGS

The accompanying drawings are incorporated by reference and form part of this specification. The drawings illustrate examples of embodiments of the invention and, together with the description, serve to explain principles of the invention. The drawings are schematic, may not be to scale, and are not intended to limit the invention to the precise arrangements shown. Identical reference numerals denote corresponding elements throughout.

FIG. 2 illustrates an ear-worn housing and sensor placement with respect to an ear-frame coordinate system.

FIG. 3 is a diagram illustrating optional implantable interfaces, including a cochlear stimulation interface and a vestibular stimulation interface.

FIG. 6 is a schematic illustrating motion-event detection (including gait-related events) and safety gating logic.

FIG. 8 is a flow diagram illustrating a clinician fitting and calibration user interface process.

FIG. 9 is a schematic illustrating an exemplary manufacturing, characterization, and calibration parameter provisioning process.

FIG. 11 is a diagram illustrating an interoperability and synergy architecture between Ear-Worn Inertial-Acoustic Fusion with Deterministic Audio-IMU Synchronization and a Steerable Interaural-Baseline Acoustic Gaze Apparatus for Assistive Listening.

FIG. 12 is a schematic depicting accessory form factors for the Steerable Interaural-Baseline Acoustic Gaze Apparatus for Assistive Listening and ear-associated inertial modules, including wearable, stick/bar, glasses, hat, and garment attachment configurations.

FIG. 13 is a diagram illustrating a combined calibration routine for aligning the Steerable Interaural-Baseline Acoustic Gaze Apparatus for Assistive Listening acoustic geometry with ear-frame inertial axes.

FIG. 14 is a schematic illustrating an assistive routing mode for unilateral impairment, including routing to a selected ear.

FIG. 15 illustrates integration into external systems (AR/VR, mobile devices, safety monitoring).

FIG. 16 illustrates a closed-loop stimulation map update based on measured perceptual outcomes and safety bounds.

FIG. 17 illustrates redundant sensing/fault detection for safety-critical operation.

DETAILED DESCRIPTION OF EMBODIMENTS

The following description is illustrative only and not limiting; the claims (and equivalents) define the scope, and nothing herein is an admission of prior art.

As used herein, "ear-associated" is to be interpreted broadly to include ear-worn, ear-mounted, in-ear, and/or implant-associated devices, and systems comprising combinations thereof. In a narrower sense, "ear-associated" may refer to an in-ear canal device having a housing retained by the concha and/or ear canal.

As used herein, an "inertial sensing subsystem" includes any sensor arrangement capable of generating motion-related data. In a narrower sense, the inertial sensing subsystem comprises a multi-axis gyroscope configured to output angular rate and, optionally, a multi-axis accelerometer configured to output linear acceleration. The inertial sensing subsystem may further include magnetometers, barometers, and/or other sensors, whether integrated or discrete.

"Deterministic synchronization" refers broadly to reproducible and computably correct alignment between inertial samples and audio samples; narrowly, it includes maintaining a mapping function from inertial timestamps to audio sample indices that remains valid across sleep/wake and power-gated transitions, including compensation for known latencies.

"World-locked" or "stabilized" refers broadly to spatial parameters that are invariant (within tolerance) to head motion; narrowly, it includes a transform that expresses a direction parameter in a world-frame coordinate system estimated from inertial integration and/or external references.

As used herein, "Steerable Interaural-Baseline Acoustic Gaze Apparatus for Assistive Listening" refers to an external binaural steering accessory comprising, in certain embodiments, a left unit and a right unit separated by an approximate interaural distance and configured to acquire directionality and/or route audio to a selected ear, including by rotation about a central region and/or by end-mounted elements. The accessory may be handheld, wearable, or integrated into an article of apparel or an electronic device.

Figure 1:
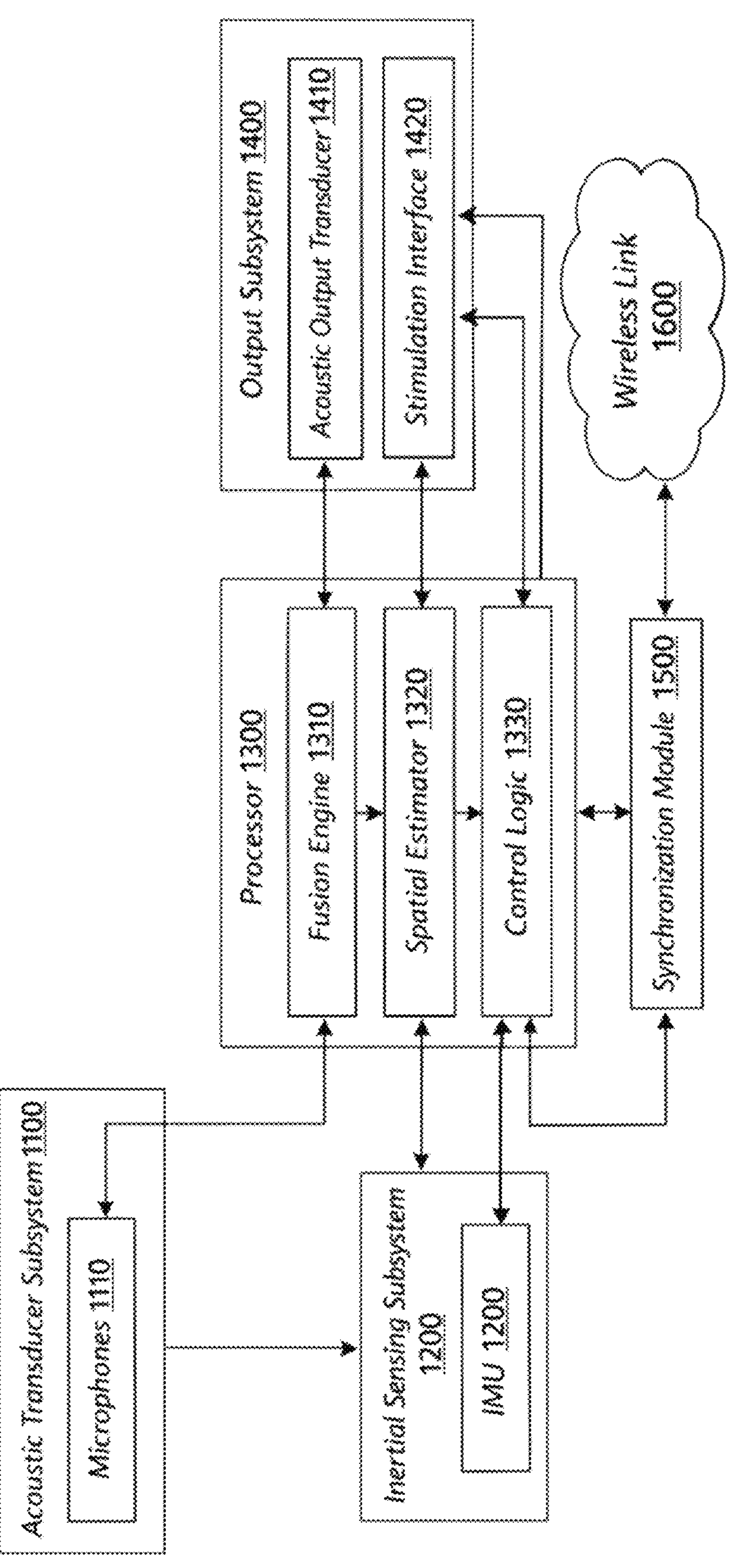
FIG. 1 illustrates a block diagram of an ear-associated inertial-acoustic fusion system.

FIG. 1 (System Overview and Functional Block Diagram): System 1000 comprises an Acoustic Transducer Subsystem 1100, an Inertial Sensing Subsystem (IMU) 1200, a Processor 1300, an Output Subsystem 1400, a Synchronization Module 1500, and a Wireless Link 1600. Acoustic Transducer Subsystem 1100 includes one or more Microphones 1110 configured to acquire environmental sound and generate one or more microphone signals, optionally including multi-channel signals for direction-related processing. IMU 1200 is configured to generate inertial measurements including, without limitation, angular rate and linear acceleration. Processor 1300 is communicatively coupled to Acoustic Transducer Subsystem 1100 and IMU 1200 and is configured to execute processing pipelines, which may be implemented in hardware, software, firmware, or any combination thereof. Processor 1300 comprises (or executes) a Fusion Engine 1310 configured to fuse inertial measurements and audio features into temporally aligned multimodal state data, a Spatial Estimator 1320 configured to determine one or more spatial parameters from audio and inertial information (including direction parameters and/or head-motion state), and Control Logic 1330 configured to select operating modes, enforce safety rules, and supervise outputs. Synchronization Module 1500 is configured to maintain deterministic temporal alignment between inertial data and audio data by associating inertial samples with a clock value, tagging audio frames with corresponding clock values, and storing or computing a translation function that maps inertial sample times to corresponding audio sample indices; in certain embodiments, the translation function is updated during operation to compensate for latency, buffer variability, clock drift, and/or oscillator tolerance. Output Subsystem 1400 is configured to generate one or more outputs based on the spatial parameters and/or control state, and includes an Acoustic Output Transducer 1410 configured to render audio and a Stimulation Interface 1420 configured to deliver stimulation outputs; Stimulation Interface 1420 may comprise an implantable stimulation interface. Wireless Link 1600 is configured to exchange configuration data, telemetry, logs, and/or software updates with one or more external devices. Signal-flow arrows illustrate: (i) Microphones 1110 to Processor 1300; (ii) IMU 1200 to Synchronization Module 1500 and to Processor 1300; (iii) Synchronization Module 1500 to Fusion Engine 1310; (iv) Fusion Engine 1310 to Spatial Estimator 1320; (v) Spatial Estimator 1320 to Control Logic 1330; and (vi) Control Logic 1330 to Output Subsystem 1400 for generation of either acoustic output via Acoustic Output Transducer 1410 or stimulation output via Stimulation Interface 1420, optionally with bidirectional status, bounds, and fault signaling from Output Subsystem 1400 back to Control Logic 1330. Optional bidirectional communications through Wireless Link 1600 are shown coupling to Processor 1300 and/or Control Logic 1330 for configuration governance, parameter provisioning, monitoring, and log export.

FIG. 2 (Ear-Worn Mechanical Integration and Coordinate Definition): An ear-worn Housing 2000 is positioned relative to anatomical features including Ear Canal 2010 and Concha 2020. Housing 2000 includes a plurality of Microphone Ports 2030 that acoustically couple ambient sound to Microphones 1110 of Acoustic Transducer Subsystem 1100. IMU 1200 is mounted within Housing 2000 in a fixed mechanical relationship to Microphones 1110, thereby establishing an ear-frame coordinate system. Ear-Frame Axes EFx, EFy, EFz are depicted as an orthogonal coordinate triad fixed to Housing 2000, representing a mechanical reference frame to which IMU 1200 sensing axes and Microphones 1110 geometry are related; the ear-frame coordinate system may be implicit as determined by mechanical design and/or explicit as defined by calibration parameters. The figure illustrates representative port placement about Housing 2000, showing that Microphone Ports 2030 may be spaced to support direction estimation and/or multi-microphone processing relative to Ear-Frame Axes EFx, EFy, EFz. The figure further illustrates that repeatable seating of Housing 2000 within Concha 2020 and proximate to Ear Canal 2010 supports consistent use of the ear-frame by Spatial Estimator 1320 and Synchronization Module 1500.

FIG. 3 (Implantable/Stimulative Outputs and Anatomical Targets): Cochlear Stimulation Interface 3000 includes Electrode Array 3010 positioned in Cochlea 3020 and coupled to stimulation drive electronics (Stimulation Circuits 3030) for generation of controlled stimulation waveforms. In certain embodiments, Stimulation Circuits 3030 are configured to generate stimulation pulses in accordance with stimulation parameters, such as current amplitude, pulse width, stimulation rate, and electrode selection. Vestibular Stimulation Interface 3100 includes Vestibular Electrodes 3110 positioned to stimulate structures associated with Semicircular Canals 3120 and coupled to corresponding drive electronics (Stimulation Circuits 3130). In certain embodiments, stimulation patterns delivered by Stimulation Circuits 3130 and Vestibular Electrodes 3110 are derived from inertial data generated by IMU 1200, optionally following transformation into an anatomical reference frame and application of an encoding function; the embodiments are not limited to any particular electrode geometry or surgical approach. The figure distinguishes cochlear stimulation and vestibular stimulation paths and depicts that Stimulation Interface 1420 (FIG. 1) may electrically couple to Cochlear Stimulation Interface 3000 and/or Vestibular Stimulation Interface 3100. Interconnects within the figure illustrate channels from Stimulation Circuits 3030 and/or Stimulation Circuits 3130 to selected electrodes of Electrode Array 3010 and/or Vestibular Electrodes 3110. The figure further illustrates that output generation is controlled by Control Logic 1330 (FIG. 1) subject to clinician-defined and/or patient-specific bounds and safety gating, including enforcement of safety constraints such as maximum amplitude, maximum charge per phase, maximum duty cycle, ramp-rate limits, and lockout behavior during detected fault conditions, where such limits may be applied prior to stimulation generation, during stimulation generation, and/or as a supervisory layer that monitors stimulation outputs and transitions the system to a bounded or safe state upon detection of a fault or out-of-range condition.

Figure 4:
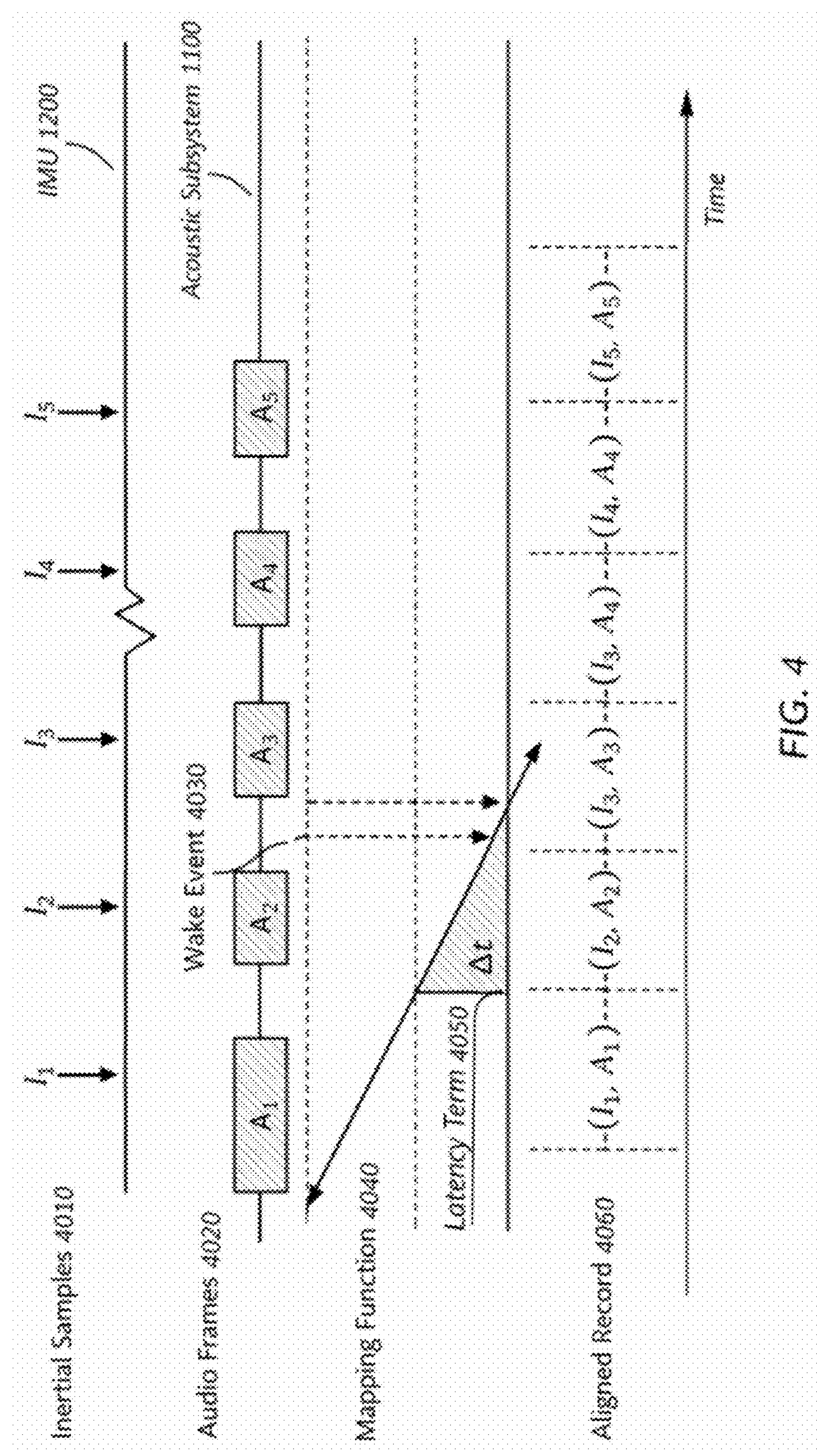
FIG. 4 is a schematic illustrating deterministic synchronization between inertial sampling and audio sampling across power-state transitions.

FIG. 4 (Deterministic Synchronization and Wake-Mapping Timing Diagram): A time-alignment schematic shows Inertial Samples 4010 produced by IMU 1200 and Audio Frames 4020 produced from Microphones 1110 and/or Acoustic Transducer Subsystem 1100. Synchronization Module 1500 maintains deterministic temporal alignment between the inertial stream and the audio stream by associating Inertial Samples 4010 with a clock value and tagging Audio Frames 4020 with corresponding clock values. A Wake Event 4030 delineates a transition in which at least a portion of audio processing may be duty-cycled and/or powered down while IMU 1200 remains active, and subsequently resumes operation. Mapping Function 4040 is illustrated as a deterministic translation function that maps inertial sample times (associated with Inertial Samples 4010) to corresponding audio sample indices and/or corresponding locations within Audio Frames 4020. Latency Term 4050 is depicted as one or more stored, measured, estimated, or bounded latency parameters incorporated into Mapping Function 4040, including parameters that account for wake latency, buffering delays, and processing delays; in certain embodiments, Mapping Function 4040 and/or Latency Term 4050 are updated during operation to compensate for latency, buffer variability, clock drift, jitter, and/or oscillator tolerance. Aligned Record 4060 is depicted as a combined record in which each inertial sample is paired with a corresponding audio frame index (or audio time) according to Mapping Function 4040 and Latency Term 4050, thereby enabling Fusion Engine 1310 to treat the inertial stream and the audio stream as sharing a unified time base across power states.

Figure 5:
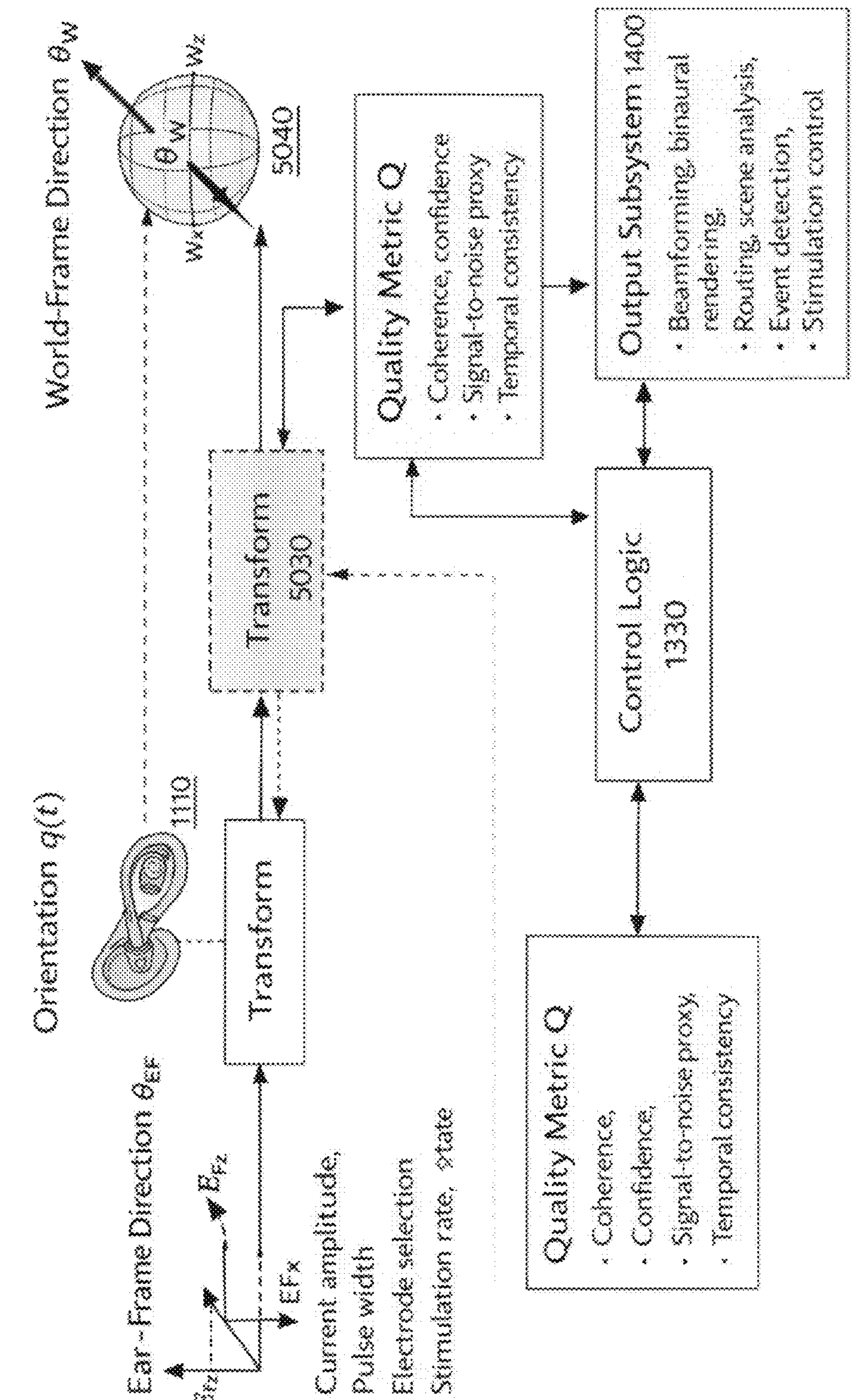
FIG. 5 is a diagram depicting the computation of stabilized world-frame spatial parameters (world-locked auditory scene).

FIG. 5 (Spatial Stabilization Computation in Ear Frame and World Frame): A block-and-arrow representation of stabilized spatial parameter computation includes Ear-Frame Direction OEF 5010 derived from one or more Microphones 1110 within Acoustic Transducer Subsystem 1100 and expressed in the ear-fixed reference associated with Ear-Frame Axes EFx, EFy, EFz. Orientation q(t) 5020 is derived from IMU 1200 and may be provided directly from inertial integration and/or from Fusion Engine 1310 as a fused estimate. Transform 5030 represents a coordinate transformation computed from Orientation q(t) 5020 and applied to Ear-Frame Direction OEF 5010 to obtain World-Frame Direction θW 5040, where θW 5040 represents a stabilized direction estimate in a world-referenced frame compensating for head motion and rotation of Housing 2000. Quality Metric Q 5050 is shown as an accompanying measure computed from one or more factors including, without limitation, coherence, confidence, signal-to-noise proxy, and/or temporal consistency, and is provided alongside World-Frame Direction θW 5040 for downstream use. The figure depicts that World-Frame Direction θW 5040 (optionally together with Quality Metric Q 5050) may be used by Control Logic 1330 and/or Output Subsystem 1400 for beamforming, binaural rendering, routing, scene analysis, event detection, and/or stimulation control, and further depicts that Transform 5030 may be continuously updated based on Orientation q(t) 5020 such that θW 5040 remains stable as OEF 5010 changes due to head motion.

FIG. 6 (Event Detection, Safety Gating, and Bounded Output Control): A control-flow schematic depicts Event Detector 6010 receiving inertial data from IMU 1200 (and optionally other signals) and generating Gait Event 6020, which may represent detection of a gait-correlated motion condition and/or another motion event detected using periodicity, acceleration signatures, and/or other features. Detected events may be used to gate processing, adjust adaptation rates, and/or mitigate motion-related artifacts. Safety Gate 6030 receives the Gait Event 6020 indicator and enforces Clinician Bounds 6050 and/or patient-specific profiles to regulate system behavior. Safety Gate 6030 outputs Bounded Output 6040 as a command and/or constrained setpoint that limits or modifies output generated by Output Subsystem 1400, including limiting or shaping output delivered by Acoustic Output Transducer 1410 and/or Stimulation Interface 1420. The figure shows that Safety Gate 6030 may apply different bounds from Clinician Bounds 6050 depending on the presence, duration, and/or confidence of Gait Event 6020 and/or depending on Quality Metric Q 5050 (FIG. 5). In response to a detected motion event and/or a reduced Quality Metric Q 5050, the figure further illustrates that the system may apply one or more gating rules, including freezing selected beamformer coefficients, increasing artifact suppression, limiting stimulation amplitude, reducing gain, and/or transitioning to a bounded-output or safe mode, and may provide supervisory feedback to Control Logic 1330 to transition between normal and bounded operating modes.

Figure 7:
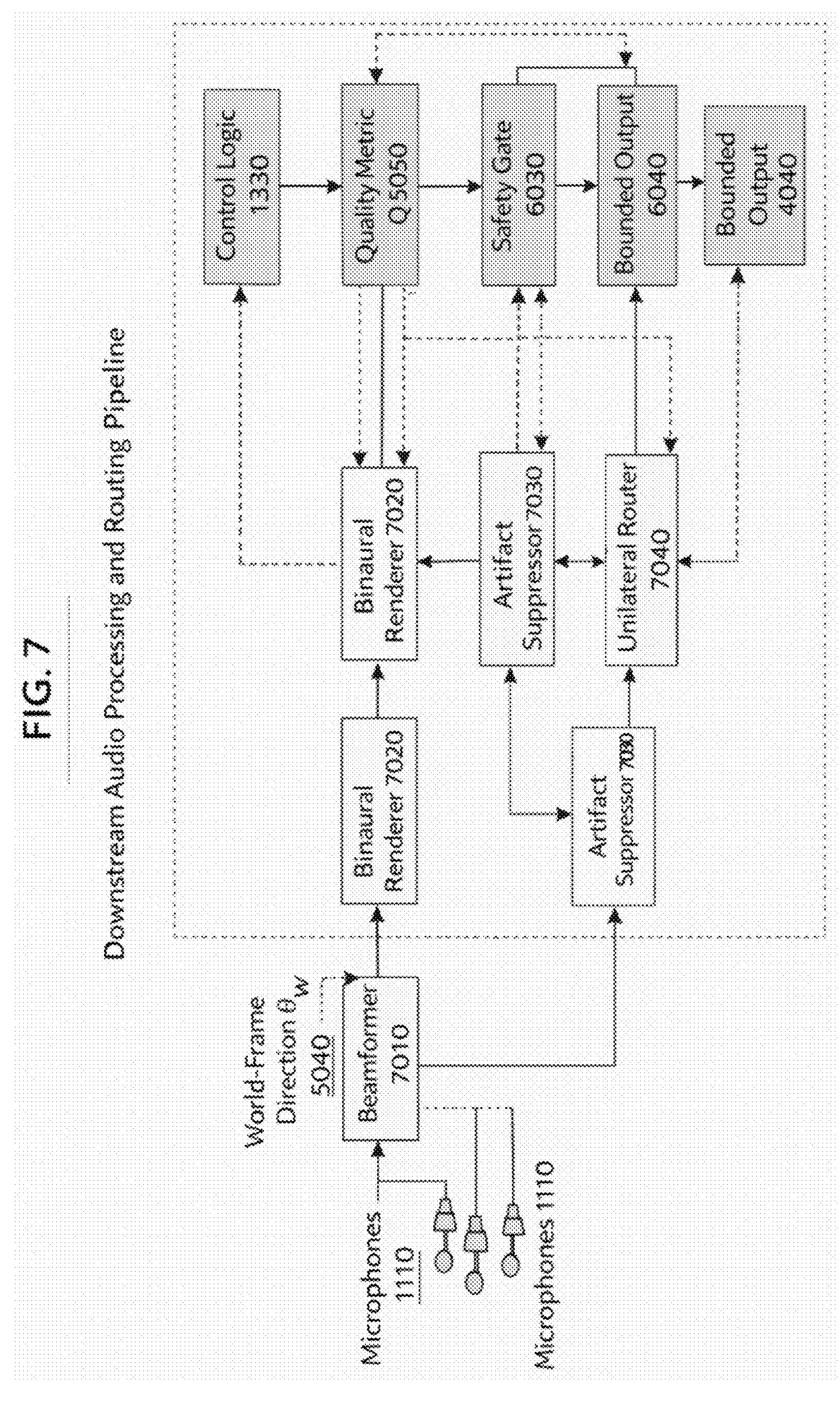
FIG. 7 is a block diagram of exemplary signal-processing modules, including beamforming, binaural rendering, and artifact suppression.

FIG. 7 (Downstream Audio Processing and Routing Pipeline): A processing pipeline depicts Beamformer 7010 receiving microphone signals from Microphones 1110 and spatial parameters including World-Frame Direction θW 5040 and producing a directionally enhanced audio signal, where Beamformer 7010 may be steered based on θW 5040 such that perceived source location is preserved while the user turns their head. Binaural Renderer 7020 receives audio from Beamformer 7010 (or directly from Microphones 1110) and renders a binauralized output suitable for presentation via Acoustic Output Transducer 1410. Artifact Suppressor 7030 receives audio and/or inertial-derived indicators (including, in certain embodiments, motion events and/or gating states) and reduces artifacts correlated with motion, wind, or other disturbances. Unilateral Router 7040 receives a processed signal and applies routing control to deliver content to one side, one output path, or one selected output endpoint, including routing to Acoustic Output Transducer 1410 such that a user with unilateral impairment may receive directional content in a functioning ear as selected via Selected Ear 14020 and Routing Control 14030 (FIG. 14), and/or including influencing operation of Stimulation Interface 1420 in stimulation embodiments. Interconnects depict that Control Logic 1330 may modulate parameters of Beamformer 7010, Binaural Renderer 7020, Artifact Suppressor 7030, and Unilateral Router 7040 based on Quality Metric Q 5050 and/or Safety Gate 6030 outputs, including applying safety gating rules that freeze selected beamformer coefficients, increase artifact suppression, limit stimulation amplitude, reduce gain, and/or transition to bounded-output operation under Bounded Output 6040.

Figure 18:
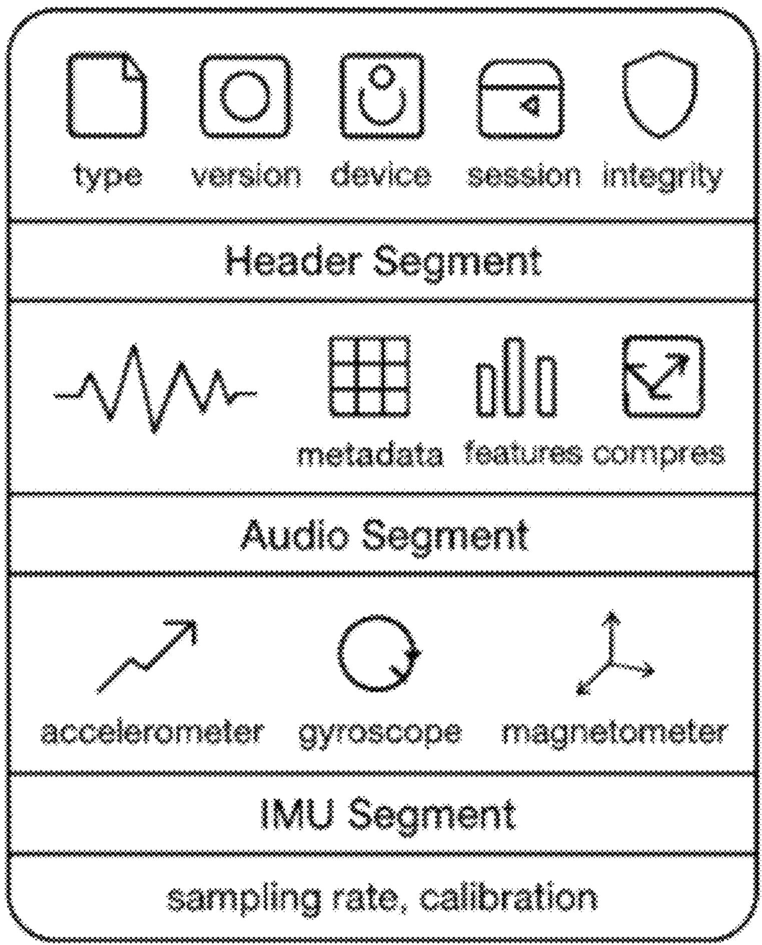
FIG. 18 illustrates a data record format for evidence-grade logging (time-aligned IMU+audio+derived parameters).

FIG. 8 (Clinician/User Configuration Workflow and Interface Functions): A workflow diagram shows a configuration and verification sequence including Pairing 8010 between System 1000 and an external device via Wireless Link 1600. Calibration 8020 establishes device- and/or user-specific calibration parameters relating Microphones 1110 geometry, Ear-Frame Axes EFx, EFy, EFz, and IMU 1200 axes, thereby supporting operation of Spatial Estimator 1320 and Synchronization Module 1500; calibration parameters may include, without limitation, an IMU-to-ear-frame rotation matrix, microphone position offsets, acoustic transfer characteristics, and latency parameters. Stabilization Setting 8030 selects stabilization strength and/or behavior of World-Frame Direction θW 5040 computation, including selecting how Transform 5030 and/or Quality Metric Q 5050 influence downstream processing. Bounds 8040 configures Clinician Bounds 6050 and any additional constraints applied by Safety Gate 6030 and Control Logic 1330 to Output Subsystem 1400 and Stimulation Interface 1420, including constraints such as maximum amplitude, maximum charge per phase, maximum duty cycle, ramp-rate limits, and lockout behavior. Verification Test 8050 validates performance, safety behavior, and alignment, including verification of Mapping Function 4040, Latency Term 4050, and resulting Aligned Record 4060 consistency and verification of stabilized beamforming performance using θW 5040. Export 8060 exports configuration parameters, audit information, and/or logs through Wireless Link 1600, including Log Record 10070 (FIG. 10) and/or records formatted according to Header 18010, Audio Segment 18020, IMU Segment 18030, Derived Parameters 18040, and Timestamps 18050 (FIG. 18). The figure depicts that each step may be interactive and may present confirmation states, error states, retry loops, and access-controlled governance states, including, in certain embodiments, configuration governance with access controls, audit trails, and hierarchical permissions, remote lockout of software-defined configuration parameters, and audit log retention and integrity protection, and further depicts that a clinician interface 8000 may provide calibration initiation, selection of stabilization strength, stimulation bounds, event gating sensitivity, and logging export settings while a user interface may provide simplified toggles including "Stabilized Focus", "Safe Walk", and "Single-ear routing".

FIG. 9 (Manufacturing/Assembly Characterization, Alignment, and Parameter Storage): A manufacturing and provisioning schematic includes Assembly 9010 describing assembly of Housing 2000 containing Microphones 1110 and IMU 1200 in a fixed mechanical relationship that supports establishment of the ear-frame. Axis Alignment 9020 describes determination of relative orientation between IMU 1200 sensing axes and Ear-Frame Axes EFx, EFy, EFz and/or microphone array geometry and, in certain embodiments, determination of calibration parameters that align microphone geometry and any acoustic direction-of-arrival estimator axes with inertial sensor axes. Latency Characterization 9030 describes measurement and/or estimation of processing and buffering delays that contribute to Latency Term 4050 and/or Mapping Function 4040 and, in certain embodiments, measurement or bounding of wake latency used across power states. Parameter Store 9040 represents nonvolatile storage containing calibration and characterization parameters (including axis alignment parameters, microphone offsets, acoustic transfer characteristics, and latency parameters) for use by Synchronization Module 1500, Fusion Engine 1310, Spatial Estimator 1320, and Control Logic 1330. Device Identifier 9050 represents an identifier associated with a particular device instance and used to index and retrieve a correct parameter set from Parameter Store 9040 and/or associate parameters with a user profile; in certain embodiments, such parameters may be updated, replaced, and/or versioned. The figure illustrates that outputs of Axis Alignment 9020 and Latency Characterization 9030 are written to Parameter Store 9040 and associated with Device Identifier 9050, and that such stored parameters are subsequently consumed during operation and/or during Calibration 8020 (FIG. 8), including for deterministic synchronization implemented by Synchronization Module 1500 and for conversion between ear-frame and inertial frames in Transform 5030 (FIG. 5).

Figure 10:
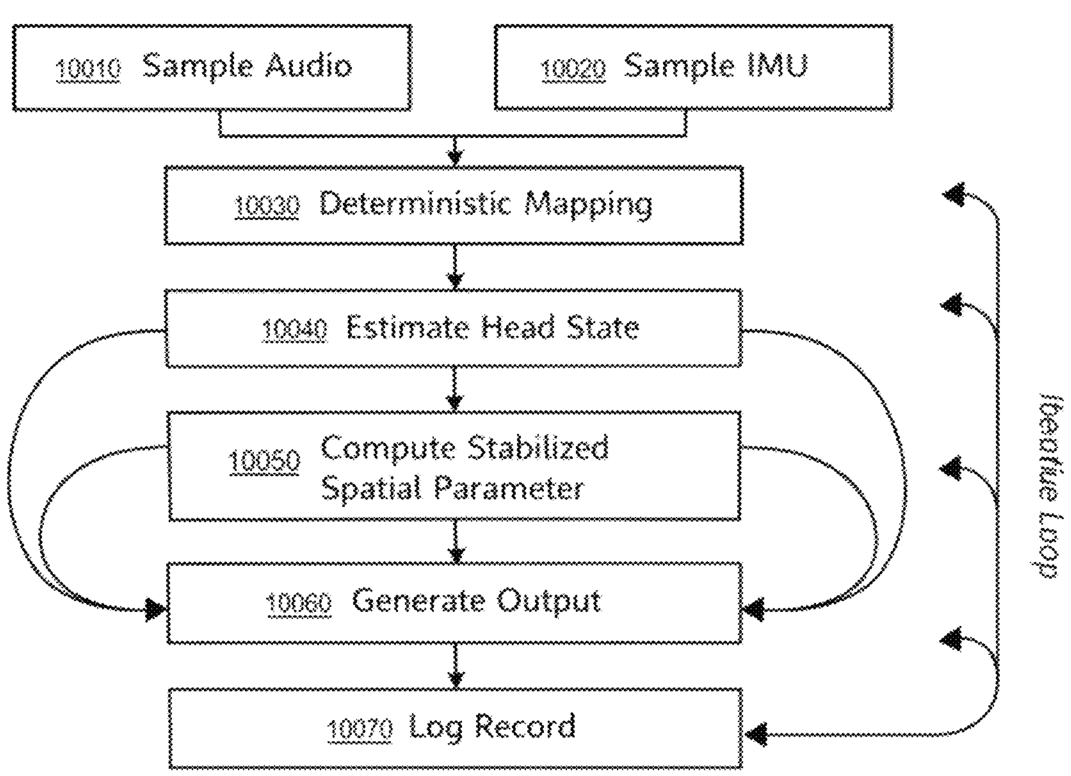
FIG. 10 is a flowchart depicting a method of ear-frame inertial-acoustic fusion with deterministic synchronization.

FIG. 10 (Method Flow for Synchronization, Estimation, Output Generation, and Logging): A method-flow diagram comprises steps including Sample Audio 10010 to acquire audio from Microphones 1110 (and optionally buffer into frames as Audio Frames 4020), and Sample IMU 10020 to acquire inertial measurements from IMU 1200 (as Inertial Samples 4010). Deterministic Mapping 10030 computes or applies Mapping Function 4040 and Latency Term 4050 to align Sample IMU 10020 with Sample Audio 10010, thereby producing synchronized inputs for Fusion Engine 1310; in one embodiment, Deterministic Mapping 10030 comprises a measured or bounded wake latency, a phase accumulator for an audio sampling clock, and a timestamp translation function that yields an audio sample index for each inertial sample time, and in certain embodiments corrects for clock drift and/or jitter so that the inertial stream and audio stream share a unified time base. Estimate Head State 10040 computes Orientation q(t) 5020 (and optionally other head-motion states) from inertial data and/or fused data. Compute Stabilized Spatial Parameter 10050 computes World-Frame Direction θW 5040 from Ear-Frame Direction θEF 5010 using Transform 5030 derived from Orientation q(t) 5020 and computes Quality Metric Q 5050; the stabilized parameters may be used for beamforming, binaural rendering, routing, scene analysis, event detection, and/or stimulation control. Generate Output 10060 drives Output Subsystem 1400, including Acoustic Output Transducer 1410 and/or Stimulation Interface 1420, optionally applying Safety Gate 6030, Clinician Bounds 6050, and other safety constraints including maximum amplitude, maximum charge per phase, maximum duty cycle, ramp-rate limits, and lockout behavior during detected fault conditions, and optionally applying rules responsive to motion events and/or reduced Quality Metric Q 5050 including freezing selected beamformer coefficients, increasing artifact suppression, limiting stimulation amplitude, reducing gain, and/or transitioning to bounded-output or safe mode. Log Record 10070 stores or transmits records including selected signals, parameters, events, bounds settings, lock/unlock state, and outcomes via Wireless Link 1600 and/or to a local log. The figure depicts iterative looping of the steps, including that Deterministic Mapping 10030, Estimate Head State 10040, and Compute Stabilized Spatial Parameter 10050 may execute continuously or periodically, and that Generate Output 10060 may be conditionally modified based on event gating and quality information while Log Record 10070 provides an auditable record of configuration and output behavior.

Figure 11:
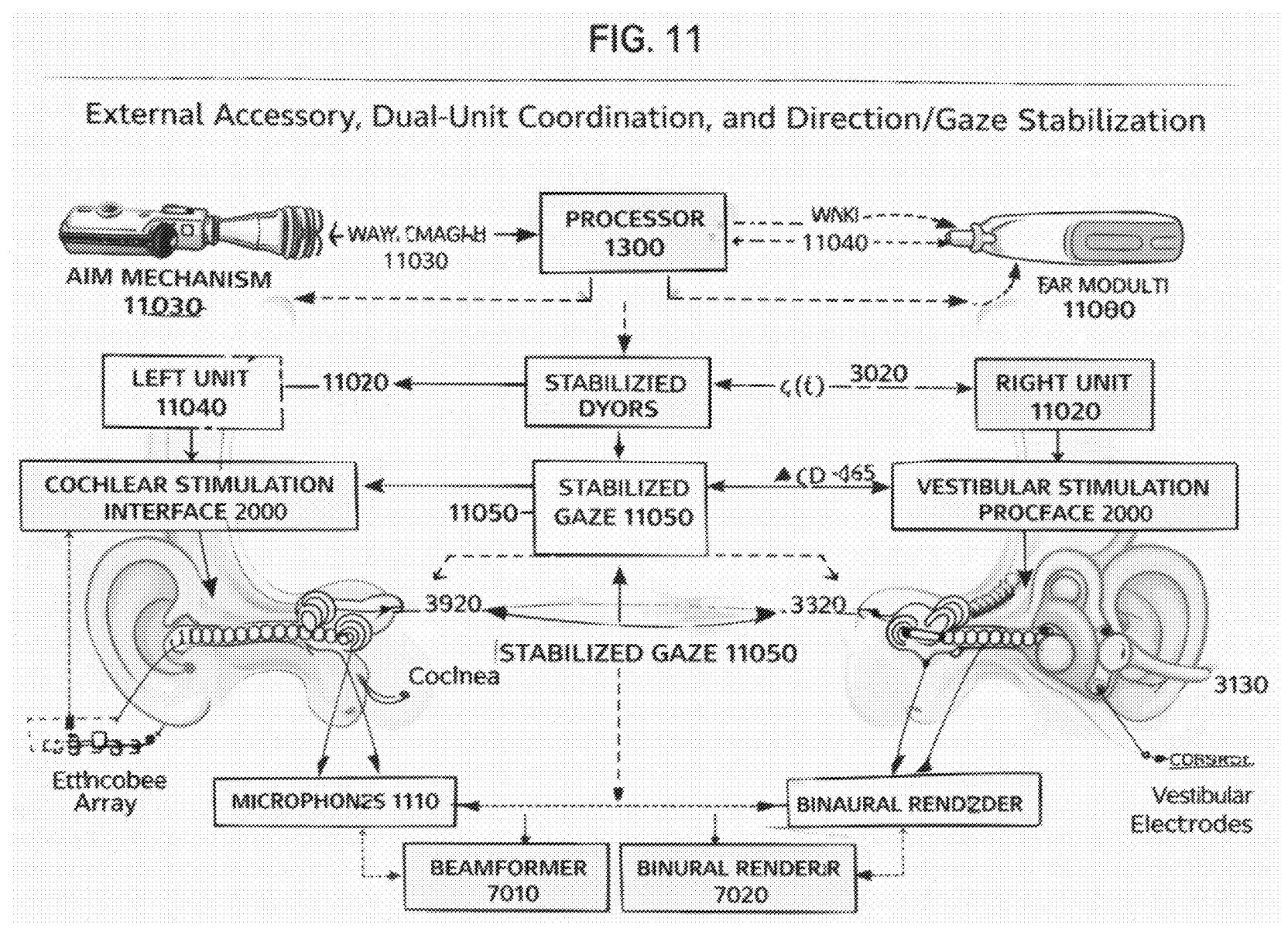

FIG. 11 (External Accessory, Dual-Unit Coordination, and Direction/Gaze Stabilization): A system-level schematic shows External Accessory 11000 in communication with Left Unit 11010 and Right Unit 11020, each unit being an instance of System 1000 or a portion thereof and each including Microphones 1110 and IMU 1200 within ear-worn Housing 2000. Aim Mechanism 11030 is shown as a user-adjustable or mount-adjustable aiming element associated with External Accessory 11000. Link 11040 is shown as a communication interface between External Accessory 11000 and one or both of Left Unit 11010 and Right Unit 11020 and, in certain embodiments, may comprise or operate through Wireless Link 1600. Ear Module 12000 is shown as an ear-worn module interacting with External Accessory 11000, where the ear-worn module provides inertial and acoustic sensing and/or output generation while External Accessory 11000 provides auxiliary aiming, user input, or coordination functions. Stabilized Gaze 11050 is shown as an output parameter representing a stabilized aim direction derived from combining Aim Mechanism 11030 state with World-Frame Direction θW 5040 and/or Orientation q(t) 5020 and, in certain embodiments, produced by Processor 1300 using Spatial Estimator 1320 and Control Logic 1330 such that motion of the user does not undesirably shift an intended aim direction. The figure depicts that Stabilized Gaze 11050 may be shared between units via Link 11040 to ensure matched spatial behavior, including matched steering of Beamformer 7010 and matched rendering via Binaural Renderer 7020, and may further be used to coordinate unilateral and/or bilateral routing behaviors via Unilateral Router 7040.

FIG. 12 (Examples of Wearable Mounts and Accessory Form Factors): Illustrative examples of wearable or mountable form factors for positioning hardware associated with System 1000 and/or External Accessory 11000 include Handheld Bar 12010, Glasses 12020, Hat 12030, Garment Clip 12040, and Wearable Accessory 12050. The figure depicts that the form factors may provide a stable mounting location for one or more sensing elements, user controls, and/or link elements, and that such mounts may be used to support alignment and aiming via Aim Mechanism 11030, pairing via Pairing 8010 through Wireless Link 1600, and/or additional sensing complementary to IMU 1200 and Microphones 1110, including providing a repeatable spatial reference for functions that utilize World-Frame Direction θW 5040.

FIG. 13 (Geometric Calibration, Axis Fitting, and Validation): A calibration schematic shows Geometry Model 13010 as a parametric or sampled model of device geometry and/or microphone/IMU pose relationships, including relationships between Microphones 1110, IMU 1200, and the ear-frame defined by Ear-Frame Axes EFx, EFy, EFz. Axis Fit 13020 represents estimation of the relationship between IMU 1200 axes and the ear-frame and/or an acoustic direction estimation axis defined by microphone geometry, thereby producing calibration parameters that align microphone geometry and any acoustic direction-of-arrival estimator axes with inertial sensor axes. Transform R 13030 represents a fitted rotation matrix (and optionally additional parameters) used by Transform 5030 and/or Spatial Estimator 1320 to relate coordinate frames, including an IMU-to-ear-frame rotation. Validation Test 13040 represents a test procedure that verifies the accuracy of Transform R 13030 and associated calibration parameters, including verifying that World-Frame Direction θW 5040 remains stable for defined motions and/or that Ear-Frame Direction OEF 5010 transforms consistently under known rotations, and may further validate that Mapping Function 4040 alignment supports consistent fusion outputs. The figure depicts that Validation Test 13040 may feed back to Axis Fit 13020 to refine Transform R 13030 and that resulting calibration parameters may be stored in Parameter Store 9040 and retrieved using Device Identifier 9050.

FIG. 14 (Unilateral Routing Based on Impairment State and Ear Selection): A control diagram shows Impairment State 14010 as a state variable describing unilateral or asymmetric hearing (or other functional) impairment. Selected Ear 14020 represents a selection output identifying the ear-side to receive routing, including selection of an ear-side for Acoustic Output Transducer 1410 delivery. Routing Control 14030 represents logic that configures Unilateral Router 7040 and/or Output Subsystem 1400 to route audio (and optionally stimulation) to the Selected Ear 14020 based on Impairment State 14010 and operating context, including applying stabilized spatial parameters such as World-Frame Direction θW 5040 to preserve directional content in the routed output. The figure depicts that Routing Control 14030 may be modulated by Quality Metric Q 5050 and safety constraints enforced by Control Logic 1330 and/or Safety Gate 6030 to avoid undesirable routing during unreliable estimation, during detected motion events including Gait Event 6020, and/or while operating under Bounded Output 6040.

FIG. 15 (External Systems Integration and Data/Control Exchanges): An ecosystem schematic illustrates System 1000 interoperating with AR/VR System 15010, Smartphone 15020, Safety System 15030, and Cloud Logging 15040. Bidirectional arrows indicate communications of configuration, real-time control, spatial parameters (including World-Frame Direction θW 5040 and Quality Metric Q 5050), telemetry, and logs via Wireless Link 1600. The figure depicts that Smartphone 15020 may host user- and/or clinician-facing configuration interfaces corresponding to Pairing 8010, Calibration 8020, Stabilization Setting 8030, Bounds 8040, Verification Test 8050, and Export 8060, including access-controlled configuration governance with audit trails, hierarchical permissions, and remote administrator and/or clinician lockout of software-defined configuration parameters. The figure further depicts that Safety System 15030 may provide external safety state inputs that gate Bounded Output 6040 and influence Safety Gate 6030 behavior, and that Cloud Logging 15040 may receive Log Record 10070 information for analysis and compliance, subject to configured export policies including selective disclosure, encrypted fields with access-controlled decryption, and integrity protection for a protected portion of an audit log.

FIG. 16 (Perceptual Feedback Loop and Bounded Adaptation): A feedback-control schematic shows Perceptual Feedback 16010 representing a user feedback signal associated with perceived spatial stability and/or comfort. Update Engine 16020 adjusts parameters used by Spatial Estimator 1320, Beamformer 7010, Binaural Renderer 7020, Artifact Suppressor 7030, Unilateral Router 7040, and/or Control Logic 1330 based on Perceptual Feedback 16010. Bounded Update 16030 represents a constrained adaptation output that applies limits and rate constraints to parameter updates. The figure depicts that Bounded Update 16030 may incorporate Clinician Bounds 6050 and may interact with Safety Gate 6030 such that updates do not violate safety constraints applicable to Output Subsystem 1400, including constraints applied to Stimulation Interface 1420 and/or constraints applied during motion-event gating and bounded-output operation.

FIG. 17 (Fault Tolerance, Monitoring, and Safe Fallback): A reliability schematic shows Redundancy 17010 representing redundant computations, redundant sensing, and/or redundant parameter checks across Processor 1300 modules including Synchronization Module 1500 functions, Fusion Engine 1310, Spatial Estimator 1320, and Control Logic 1330. Watchdog 17020 represents a supervisory monitor that detects stalls, out-of-range values, inconsistent mappings, or other fault conditions, including fault conditions relating to deterministic temporal alignment, Mapping Function 4040 validity, latency bounds, and/or safety limit enforcement. Safe Fallback 17030 represents a defined safe operational state entered upon detection of a fault, including disabling or constraining outputs under Bounded Output 6040 and/or reverting to a conservative processing mode that maintains safe operation of Output Subsystem 1400 and Stimulation Interface 1420. The figure depicts that Watchdog 17020 provides a trigger to Safe Fallback 17030 and optionally records fault information and mode-transition information to Log Record 10070 and/or to an audit log subject to retention and integrity protection.

FIG. 18 (Data Record Structure for Logging and Export): A data-structure schematic shows a record format including Header 18010 identifying record type, device association, and versioning, and optionally identifying a Device Identifier 9050 association. Audio Segment 18020 contains one or more audio frames and/or derived audio features associated with Sample Audio 10010 and Audio Frames 4020. IMU Segment 18030 contains inertial samples associated with Sample IMU 10020 and Inertial Samples 4010. Derived Parameters 18040 includes computed values such as Ear-Frame Direction OEF 5010, Orientation q(t) 5020, World-Frame Direction θW 5040, Quality Metric Q 5050, and event indicators such as Gait Event 6020 and bounded-output state. Timestamps 18050 include timestamps or indices sufficient to reconstruct Deterministic Mapping 10030, Mapping Function 4040, Latency Term 4050, and associated alignment relationships, including wake-related mapping across Wake Event 4030 where relevant. The figure depicts that the record may be exported via Export 8060 through Wireless Link 1600 to Smartphone 15020 and/or Cloud Logging 15040, may support audit trails and configuration governance, and may support selective disclosure and privacy-preserving verification by employing integrity protection and/or encrypted fields with access-controlled decryption, thereby enabling redaction of selected fields while preserving verifiable integrity.

System Architecture

The system comprises an acoustic transducer subsystem, which includes one or more microphones, an inertial sensing subsystem, a processor, and an output subsystem. The output subsystem may comprise an acoustic output transducer (for example, a receiver or speaker) and/or an implantable stimulation interface. The processor may execute one or more functional modules, including, without limitation, an inertial-acoustic fusion engine, a spatial estimator, and control logic. Such modules may be implemented in hardware, software, firmware, or any combination thereof.

The system further includes a synchronization module configured to maintain deterministic temporal alignment between inertial data and audio data. In certain embodiments, the synchronization module associates inertial samples with a clock value, tags audio frames with corresponding clock values, and stores or computes a translation function that maps inertial sample times to corresponding audio sample indices. In certain embodiments, the translation function is updated during operation to compensate for latency, buffer variability, clock drift, and/or oscillator tolerance.

Ear-Frame Definition, Mechanical Integration, and Calibration

In one embodiment, the inertial sensing subsystem is mounted in a fixed mechanical relationship to the one or more microphones within an ear-worn housing, thereby establishing an ear-frame coordinate system. The ear-frame coordinate system may be implicit, as determined by mechanical design, and/or explicit, as defined by calibration parameters.

During manufacturing, characterization, and/or fitting (for example, as illustrated in FIG. 9), calibration parameters may be determined to align (i) microphone geometry and any acoustic direction-of-arrival estimator axes with (ii) inertial sensor axes. Calibration parameters may include, without limitation, a rotation matrix (e.g., IMU-to-ear-frame), microphone position offsets, acoustic transfer characteristics, and latency parameters. Such calibration parameters may be stored in nonvolatile memory associated with a device identifier and/or a user profile, and may be updated, replaced, or versioned as necessary.

Optional Implantable Stimulation Interfaces and Safety Limits

In certain embodiments, the output subsystem comprises a cochlear stimulation interface including an electrode array and a stimulation circuit configured to generate stimulation pulses in accordance with stimulation parameters, such as current amplitude, pulse width, stimulation rate, and electrode selection.

In certain embodiments, the output subsystem further or alternatively comprises a vestibular stimulation interface including one or more electrodes configured to stimulate vestibular pathways. In such embodiments, stimulation patterns may be derived from inertial data, optionally following transformation into an anatomical reference frame and application of an encoding function. The embodiments described herein are not limited to any particular electrode geometry or surgical approach.

In embodiments supporting stimulation, the control logic may enforce safety constraints, including, without limitation, maximum amplitude, maximum charge per phase, maximum duty cycle, ramp-rate limits, and lockout behavior during detected fault conditions. Clinician-defined bounds and patient-specific profiles may be used to parameterize one or more safety constraints. Safety limits may be applied prior to stimulation generation, during stimulation generation, and/or as a supervisory layer that monitors stimulation outputs and transitions the system to a bounded or safe state upon detection of a fault or out-of-range condition.

Deterministic Synchronization Across Power States

In one embodiment, the system operates in a low-power mode in which the inertial sensing subsystem remains active while portions of audio processing are duty-cycled and/or powered down. Upon a wake condition, the synchronization module computes a deterministic mapping between inertial samples collected during the low-power mode and audio frames collected after wake, utilizing stored or estimated latency parameters and/or synchronization markers.

In one embodiment, the mapping comprises: (a) a measured or bounded wake latency; (b) a phase accumulator for an audio sampling clock; and (c) a timestamp translation function that yields an audio sample index for each inertial sample time. In certain embodiments, the mapping corrects for clock drift and/or jitter and enables a downstream fusion pipeline to treat the inertial stream and the audio stream as sharing a unified time base.

Computation of Stabilized Spatial Parameters

In one embodiment, the spatial estimator computes a direction parameter from the one or more microphones and computes a head-motion state from inertial data (for example, angular rate and/or orientation). A stabilized direction parameter may then be computed in a world frame by applying an estimated orientation to transform an ear-frame direction estimate into the world frame. The stabilized parameters may be used for beamforming, binaural rendering, routing, scene analysis, event detection, and/or stimulation control.

The stabilized direction parameter may be output together with a quality metric (for example, coherence, confidence, signal-to-noise proxy, and/or temporal consistency). In certain embodiments, one or more downstream processing actions are enabled, weighted, or inhibited based on the quality metric.

Motion Events and Safety Gating

In one embodiment, the control logic detects motion events from the inertial data stream, including head impulses and/or gait-correlated events, utilizing periodicity and acceleration signatures and/or other features. Detected events may be used to gate processing, to adjust adaptation rates, and/or to mitigate motion-related artifacts.

In response to a detected motion event and/or a reduced quality metric, the system may apply one or more safety gating rules, including, without limitation, freezing selected beamformer coefficients, increasing artifact suppression, limiting stimulation amplitude, reducing gain, and/or transitioning to a bounded-output or safe mode.

Examples of Operation and User Interfaces Example A—stabilized beamforming: the system computes a stabilized θW and steers a beamformer toward a talker in the stabilized direction while the user turns their head, thereby preserving perceived source location. Example B—unilateral support: the system identifies a target direction and routes audio to a selected ear output transducer 1410 such that a user with unilateral impairment receives directional content in the functioning ear (FIG. 14).

Example C—Vestibular support: in an embodiment with a vestibular interface 3100, inertial data is converted to stimulation patterns emulating canal-like encoding, subject to clinician-set limits and safety gating. Vestibular implants are currently under clinical investigation, underscoring the need for safe and controllable stimulation algorithms.

Clinician UI (see FIG. 8): A clinician interface 8000 may provide: (i) calibration initiation, (ii) selection of stabilization strength, (iii) stimulation bounds, (iv) event gating sensitivity, and (v) logging export settings. A user interface may provide simplified toggles (for example, "Stabilized Focus", "Safe Walk", "Single-ear routing").

In certain embodiments, a clinician interface and/or management interface provides configuration governance for calibration parameters, stabilization strength, stimulation bounds, event gating sensitivity, and logging and export settings, for deployment in clinical, occupational, and consumer environments. Configuration governance may include access controls, audit trails, and hierarchical permissions.

In certain embodiments, governance is implemented via a combination of (i) a mechanical selector and (ii) a software-defined configuration. Where a mechanical selector state conflicts with a software-defined configuration, the mechanical selector may take precedence. In other embodiments, software-defined configuration may take precedence, subject to authentication and authorization.

In certain embodiments, a remote administrator and/or clinician may lock one or more software-defined configuration parameters, thereby preventing an end user from modifying such parameters via a user interface. In certain embodiments, the system stores lock state and configuration history in an audit log.

In certain embodiments, the system maintains an audit log of configuration changes, lock/unlock events, stimulation-bound changes, and/or mode-selection events. Audit log retention and clearing behavior may be selected from user-clearable, non-clearable except by an authorized administrator or clinician, tiered logging, or any combination thereof.

In certain embodiments, a protected portion of the audit log is maintained with integrity protection, which may include cryptographic signing, hash-chaining, secure hardware-backed storage (for example, secure element and/or TPM-backed storage), or any combination thereof, and is configured for local on-device verification and/or remote verification by an authorized management or fitting system.

In certain embodiments, log export supports selective disclosure and privacy-preserving verification by employing field-level commitments and/or encrypted fields with access-controlled decryption, thereby enabling redaction of selected fields while preserving verifiable integrity.

The invention claimed is:

1. An ear-associated assistive system comprising: an acoustic transducer subsystem configured to generate an audio signal; an inertial sensing subsystem configured to generate inertial data indicative of head motion; an output subsystem configured to provide an output to a user; at least one processor operatively coupled to the acoustic transducer subsystem, the inertial sensing subsystem and the output subsystem; and a synchronization module configured to maintain temporal alignment between the audio signal and the inertial data; wherein the at least one processor is configured to determine, based on the audio signal and the inertial data, a motion-compensated spatial parameter and to control the output subsystem in dependence on the motion-compensated spatial parameter.

2. The ear-associated assistive system of claim 1, wherein the acoustic transducer subsystem (1100) comprises one or more microphones (1110) and is configured to generate an audio input signal, the inertial sensing subsystem (1200) is configured to output inertial data including at least angular rate, the output subsystem (1400) comprises an acoustic output transducer (1410) and/or a stimulation interface (1420), and the synchronization module (1500) is configured to maintain deterministic temporal alignment between the inertial data and the audio input signal by maintaining a deterministic mapping (4040) between inertial sample times and audio sample indices, wherein the deterministic mapping (4040) is maintained across a power-state transition (4030), and wherein the at least one processor (1300) is configured to compute, from the inertial data, a head-motion state (5020), to compute, from the audio input signal, an ear-frame direction parameter (5010), to compute, based on the head-motion state (5020), a transformation (5030) for transforming the ear-frame direction parameter (5010) into a stabilized direction parameter (5040) expressed in a stabilized coordinate frame, and to control generation, by the output subsystem (1400), of at least one output based on the stabilized direction parameter (5040).

3. The system (1000) of claim 2, wherein the at least one processor (1300) is configured to output, together with the motion-compensated spatial parameter and/or the stabilized direction parameter (5040), a quality metric (5050) indicative of validity of the motion-compensated spatial parameter and/or the stabilized direction parameter (5040).

4. The system (1000) of claim 3, wherein the at least one processor (1300) is configured to enable, weight or inhibit at least one downstream audio processing action based on the quality metric (5050).

5. A combined assistive system comprising: the ear-associated assistive system (1000) of claim 2; and an external binaural steering accessory (11000) comprising a left acoustic unit (11010) and a right acoustic unit (11020); wherein the at least one processor (1300) is configured to stabilize a directional operation of the external binaural steering accessory (11000) in the stabilized coordinate frame based on the stabilized direction parameter (5040).

6. The combined assistive system of claim 5, wherein the at least one processor (1300) is configured to calibrate a transformation (13030) between an accessory geometry of the external binaural steering accessory (11000) and an ear-frame coordinate system (EFx, EFy, EFz) defined by an ear-worn housing (2000) of the inertial sensing subsystem (1200).

7. The system (1000) of claim 1, wherein the inertial sensing subsystem (1200) is disposed within an in-ear or ear-worn housing (2000) that defines an ear-frame coordinate system (EFx, EFy, EFz).

8. The system (1000) of claim 1, wherein the at least one processor (1300) is configured to control a beamformer (7010) in dependence on the motion-compensated spatial parameter and/or the stabilized direction parameter (5040) to generate a beamformed signal for driving the acoustic output transducer (1410).

9. The system (1000) of claim 1, wherein the stimulation interface (1420) comprises a cochlear stimulation interface (3000) including an electrode array (3010).

10. The system (1000) of claim 1, wherein the stimulation interface (1420) comprises a vestibular stimulation interface (3100) configured to stimulate vestibular pathways.

11. The system (1000) of claim 1, wherein the at least one processor (1300) is configured to generate, for driving the stimulation interface (1420), a stimulation control signal subject to at least one safety constraint including at least one of maximum amplitude, maximum charge per phase, maximum duty cycle, ramp-rate limit or lockout behaviour.

12. The system (1000) of claim 11, further comprising clinician-defined bounds (6050), wherein the at least one processor (1300) is configured to apply the clinician-defined bounds (6050) as at least part of the at least one safety constraint.

13. The system (1000) of claim 1, wherein the at least one processor (1300) is configured to detect a motion event (6020) from the inertial data and, in response to the motion event (6020) and/or a reduced quality metric (5050), control the output subsystem (1400) in accordance with a safety gating rule (6030) by limiting at least one of acoustic gain, beamformer adaptation, or stimulation amplitude.

14. The system (1000) of claim 13, wherein the safety gating rule (6030) comprises freezing selected beamformer coefficients of the beamformer (7010) and/or increasing artifact suppression (7030) during the motion event (6020).

15. A method of operating an ear-associated assistive system, the method comprising: sampling an audio signal using an acoustic transducer subsystem; sampling inertial data using an inertial sensing subsystem, the inertial data being indicative of head motion; maintaining temporal alignment between the audio signal and the inertial data; determining, based on the audio signal and the inertial data, a motion-compensated spatial parameter; and controlling generation of at least one output by an output subsystem in dependence on the motion-compensated spatial parameter.

16. The method of claim 15, wherein maintaining temporal alignment between the audio signal and the inertial data comprises maintaining deterministic temporal alignment by maintaining a deterministic mapping (4040) between inertial sample times and audio sample indices, wherein the deterministic mapping (4040) is maintained across a power-state transition (4030), and wherein determining the motion-compensated spatial parameter comprises computing, from the inertial data, a head-motion state (5020), computing, from the audio signal, an ear-frame direction parameter (5010), and applying a transformation (5030) based on the head-motion state (5020) to obtain a stabilized direction parameter (5040) expressed in a stabilized coordinate frame.

17. The method of claim 15, further comprising determining a quality metric (5050) indicative of validity of the motion-compensated spatial parameter and enabling, weighting or inhibiting at least one of beamformer processing (7010) or routing (7040) based on the quality metric (5050).

18. The method of claim 15, further comprising controlling stimulation via the stimulation interface (1420) subject to at least one safety constraint including at least one of maximum amplitude, maximum charge per phase, maximum duty cycle, ramp-rate limit or lockout behaviour.

19. A non-transitory computer-readable medium storing instructions that, when executed by at least one processor (1300) of an ear-associated assistive system (1000), cause the at least one processor (1300) to perform the method of claim 15.

20. The non-transitory computer-readable medium of claim 19, wherein the instructions cause the at least one processor (1300) to store at least one calibration parameter in a parameter store (9040) and to compute and/or update, via a synchronization module (1500), the deterministic mapping (4040) based on at least a latency parameter (4050).

* * * * *